United States Patent
Ward et al.

(10) Patent No.: US 6,590,078 B2
(45) Date of Patent: Jul. 8, 2003

(54) DNA SEQUENCES, VECTORS, AND FUSION POLYPEPTIDES FOR SECRETION OF POLYPEPTIDES IN FILAMENTOUS FUNGI

(75) Inventors: Michael Ward, San Francisco, CA (US); Scott D. Power, San Bruno, CA (US)

(73) Assignee: Genencor International, Inc., Palo Alto, CA (US)

( * ) Notice: Subject to any disclaimer, the term of this patent is extended or adjusted under 35 U.S.C. 154(b) by 14 days.

(21) Appl. No.: 09/912,733

(22) Filed: Jul. 23, 2001

(65) Prior Publication Data

US 2003/0092131 A1 May 15, 2003

Related U.S. Application Data

(62) Division of application No. 08/785,668, filed on Jan. 17, 1997, now Pat. No. 6,265,204.

(51) Int. Cl.⁷ ............................ C07K 1/00; C12P 21/04
(52) U.S. Cl. ...................................... 530/350; 435/69.7
(58) Field of Search ........................ 530/350; 435/69.1, 435/69.8, 71.1

(56) References Cited

U.S. PATENT DOCUMENTS

| 5,218,093 A | 6/1993 | Guo et al. |
| 5,242,810 A | 9/1993 | Maraganore et al. |
| 5,364,770 A | 11/1994 | Berka et al. |
| 5,679,543 A | 10/1997 | Lawlis |

FOREIGN PATENT DOCUMENTS

| EP | 0 249 350 | 12/1987 |
| EP | 316748 | 5/1989 |
| EP | 467839 | 1/1992 |
| EP | 578472 | 1/1994 |
| EP | 0591524 | 4/1994 |
| EP | 0 215 594 | 1/1995 |
| FR | 2 593 518 | 7/1987 |
| JP | 03280893 | 12/1991 |
| WO | 90/06370 | 6/1990 |
| WO | 90/15860 | 12/1990 |
| WO | 92/01797 | 2/1992 |
| WO | 92/06211 | 4/1992 |
| WO | 96/36718 | 11/1996 |

OTHER PUBLICATIONS

Altman et al., "Intracellular expression of BPTI fusion proteins and single column cleavage/affinity purification by chymotrypsin," Protein–Eng., 4(5):593–600 (1991).

Bourbonnais et al., "Secretion of Somatostatin by *Saccharomyces cerevisiae*," The Journal of Biological Chemistry, 263(30):15342–15347 (1988).

Broekhuijsen, M., et al., "Secretion of heterologous proteins by Asperguilus niger: Production of active human interleukin–6 in a protease–deficient mutant by KEX2–like processing of a glucoamylase–hIL6 fusion protein", Jour. of Biotech. 31:135–145, 1993.

Contreras, R., et al., "Efficient KEX2–like Processing of a Glucoamylase–interleukin–6 Fusion Protein by Aspergillus Nidulans and Secretion of Mature Interleukin–6", Bio/Technology vol. 9:378–381, Apr. 1991.

Evans, R., et al., "Activity and thermal stability of genetically truncated forms of *Asperigillus glucoamylase*", Gene 91:131–134, 1990.

Forsberg et al., "Thrombin and H64A Subtilisin Cleavage of Fusion Proteins for Preparation of Human Recombinant Parathyroid Hormone", Journal of Protein Chemistry, 10(5):517–526 (1991).

Gardella et al., "Expression of Human Parathyroid Hormone–(1–84) in *Escherichia coli* as a Factor X–cleavable Fusion Protein", Journal of Biological Chemistry, 265(26):15854–15859 (1990).

Gwynne, D.I. et al., "Genetically Engineered Secretion of Active Human Interferon and a Bacterial Endoglucanase from Aspergillus Nidulans", Bio/Technology., 5:713–719, (1987).

Ishizaki et al., "Production of recombinant human glucagon in the form of a fusion protein in *Escherichia coli*; recovery of glucagons by sequence–specific digestion", Appl. Microbiol. Biotechnol., 36(4):483–486 (1992).

Jeenes, D.J., et al., "A truncated glucoamylase gene fusion for heterologous protein secretion from *Aspergillus niger*", FEMS Microbiology Letters 107:267–272, 1993.

Kempe et al., "Multiple–copy genes: production and modification of monomeric peptides from large multimeric fusion proteins," Gene, 39:239–245 (1985).

Korman, D.R. et al., "Cloning, Characterization and Expression of Two α–amylase genes from *Aspergillus niger var.awamori*", Current Genetics., 17:203–212, (1990).

Kuliopulos et al., "Production, Purification, and Cleavage of Tandem Repeats of Recombinant Peptides", J. Am. Chem. Soc. 116:4599–4607 (1994).

(List continued on next page.)

Primary Examiner—Sean McGarry
Assistant Examiner—Janet Epps-Ford
(74) Attorney, Agent, or Firm—Richard F. Trecartin; Dorsey & Whitney LLP

(57) ABSTRACT

The invention includes novel fusion nucleic acids encoding fusion polypeptides which when expressed in a filamentous fungus result in the expression of fusion polypeptides. The fusion nucleic acids comprise four nucleic acids which encode a fusion polypeptide comprising first, second, third and fourth amino acid sequences. The first nucleic acid encodes a signal polypeptide functional as a secretory sequence in a first filamentous fungus. The second nucleic acid encodes a secreted polypeptide or functional portion thereof which is normally secreted from the same filamentous fungus or a second filamentous fungus. The third nucleic acid encodes a cleavable linker while the fourth nucleic acid comprises at least two nucleic acids encoding desired polypeptides.

23 Claims, 10 Drawing Sheets

OTHER PUBLICATIONS

Lennick et al., "High–level expression of α–human atrial natriuretic pept8ide from multiple joined genes in *Escherichia coli*", Gene, 61:103–112 (1987).

Libby, C. et al., "Effect of Amino Acid Deletions in the O–glycosylated Region of *Aspergillus awamori* Glucoamylase", Protein Engineering., 7(9):1109–1114, (1994).

Moks et al., "Large–Scale Affinity Purification of Human Insulin–like Growth Facto I From Culture Medium of *Escherichia Coli*", Bio/Technology, 5:379–(Apr. 1987).

Nyyssonen, E., et al., "Efficient Production of Antibody Fragments by the Filamentous Fungus Trichoderma reesei", Bio/Tech. vol. 11:591–595, May 1993.

Nyyssönen E. et al., "Protein Production by the Filamentous Fungus *Trichoderma reesei*: Secretion of Active Antibody Molecules", Can. J. Bot., 73(Supp. 1):S885–S890, (1995).

Roberts, I. N. et al., "Heterologous Gene Expression in *Aspergillus niger*: a Glucoamylase–porcine Pancreatic Prophospholipase A2 Fusion Protein is Secreted and Processed to Yield Mature Enzyme", Gene., 122:155–161, (1992).

Shen, S. "Multiple joined genes prevent product degradation in *Escherichia coli*", Proc. Natl. Acad. Sci. USA, 81:4627–4631 (Aug. 1984).

Takasuga et al., "Efficient Production of a Small Peptide by Expression as a Multimeric Form Fused with the Dihydrofolate Reductase Affinity Handle", J. Biochem, 112(5):652–657 (1992).

Tsuchiya, K., et al., "High Level Secretion of Calf Chymosin Using a Glucoamylase–prochymosin Fusion Gene in *Asperigillus oryzae*", Biosci. Biotech. Biochem. 58(5):895–899, 1994.

Ward, P.P., et al., "A System for Production of Commercial Quantities of Human Lactoferrin: A Broad Spectrum Natural Antibiotic", Bio/Tech. vol. 13:498–503, May 1995.

Ward M. et al., "Improved Production of Chymosin in Aspergillus by Expression as a Glucoamylase–Chymosin Fusion", *Bio/Technology.*, 8:435–440, (1990).

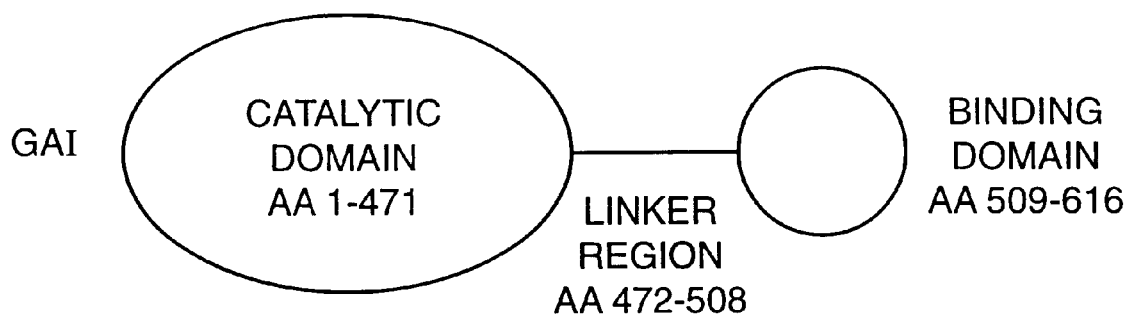
FIG._1A
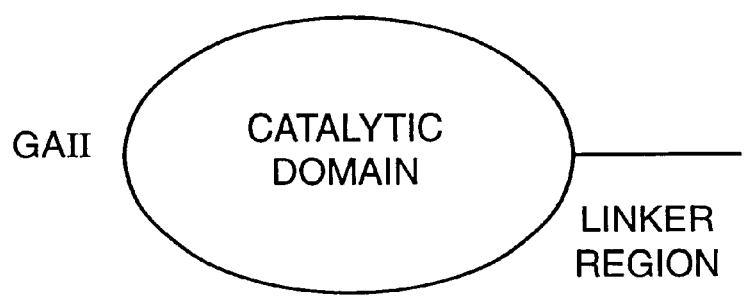
FIG._1B

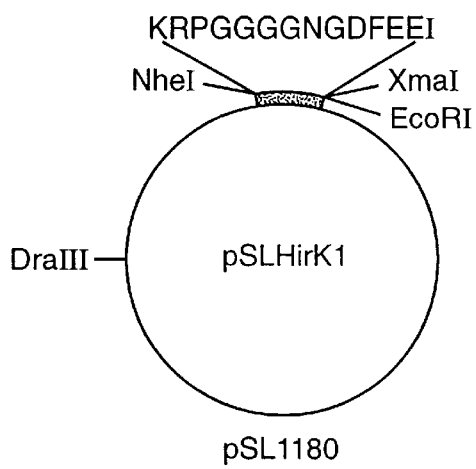
FIG._2A
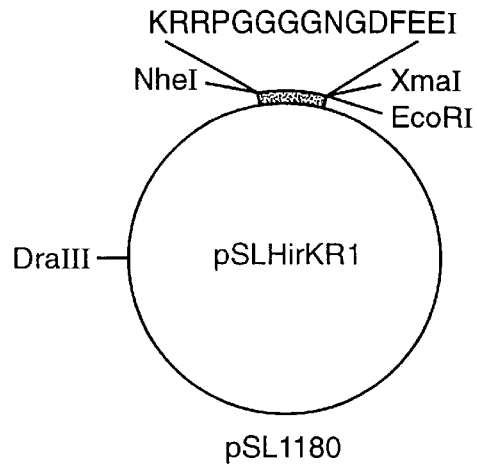
FIG._2B
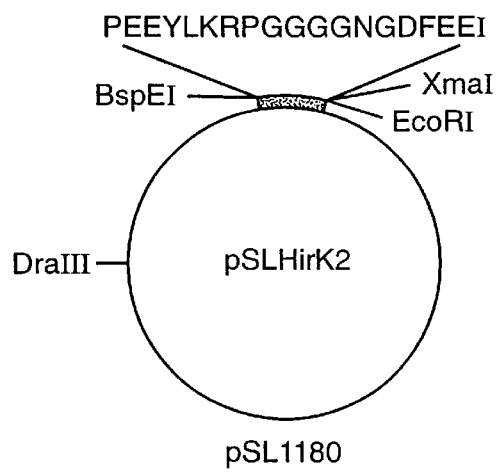
FIG._2C
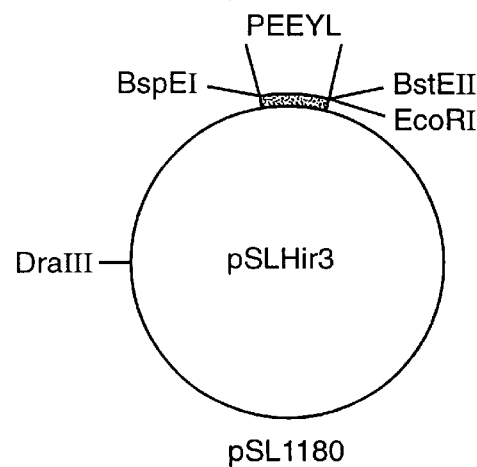
FIG._2D
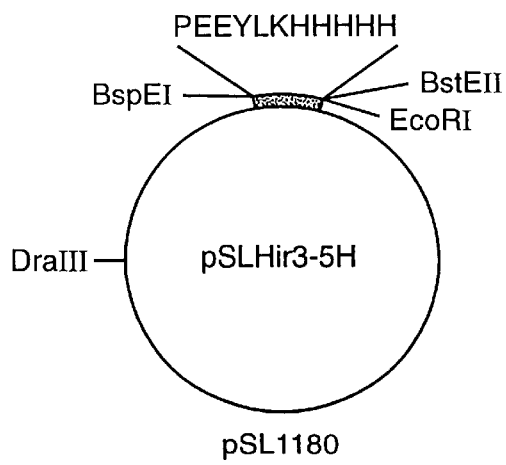
FIG._2E

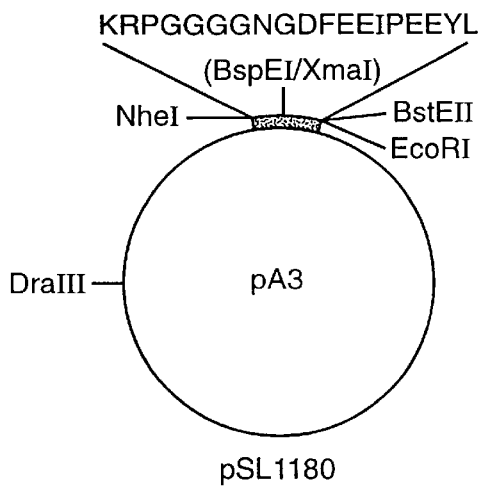
FIG._3A
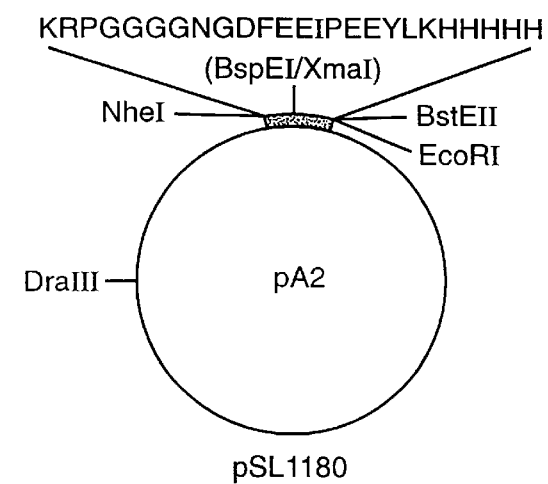
FIG._3B
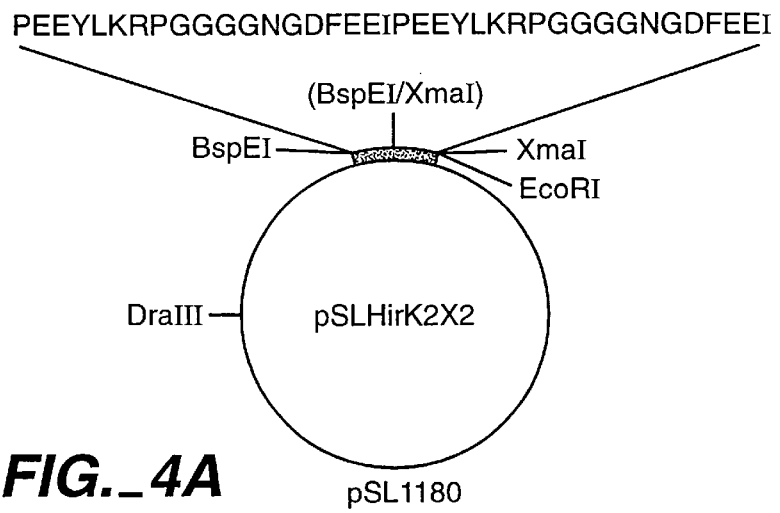
FIG._4A
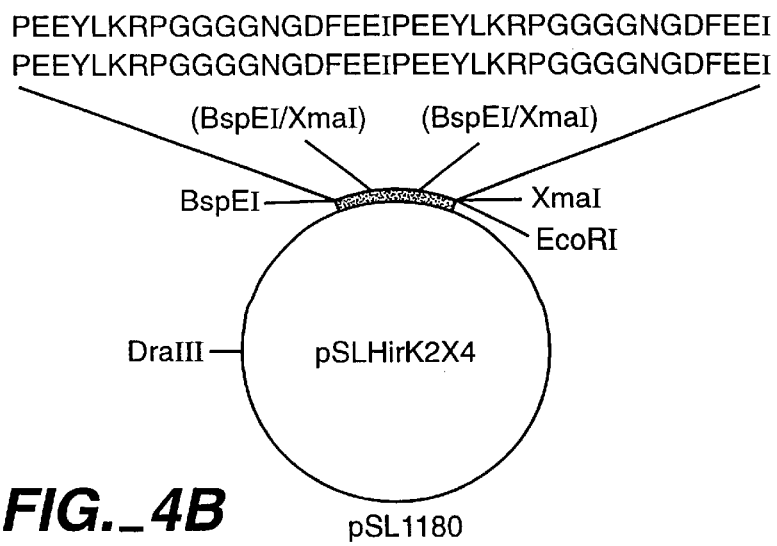
FIG._4B

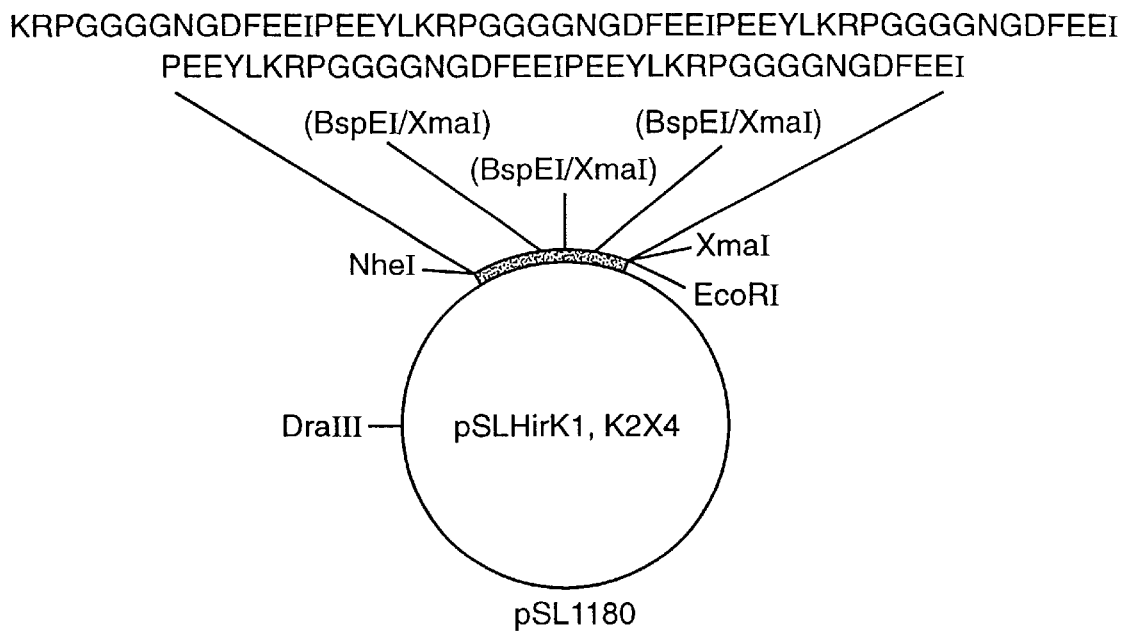
FIG._5A
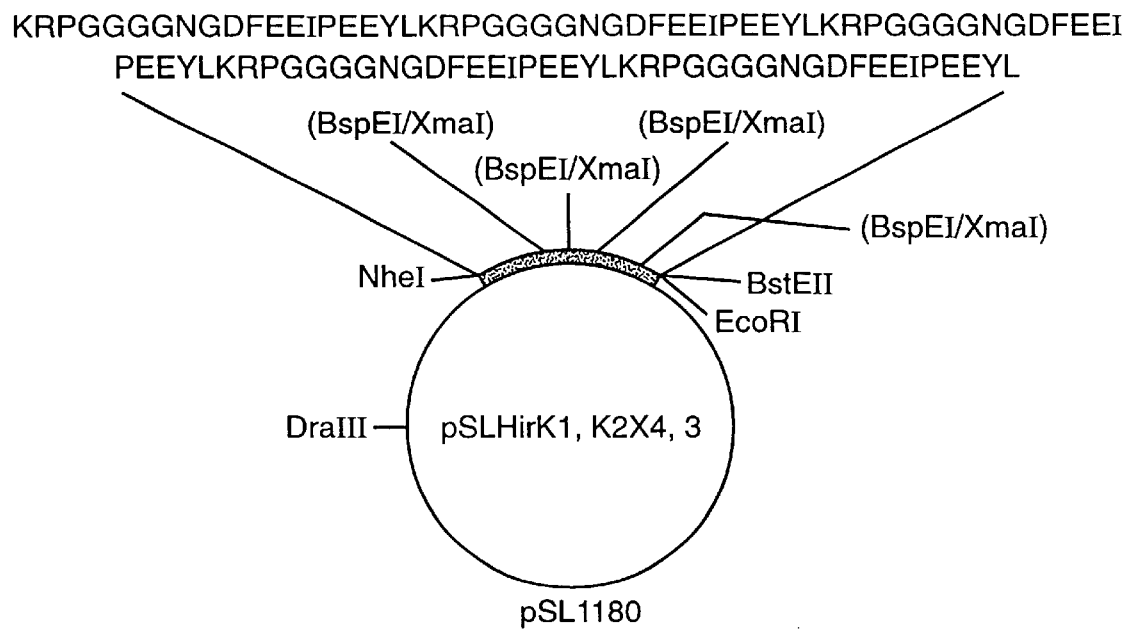
FIG._5B

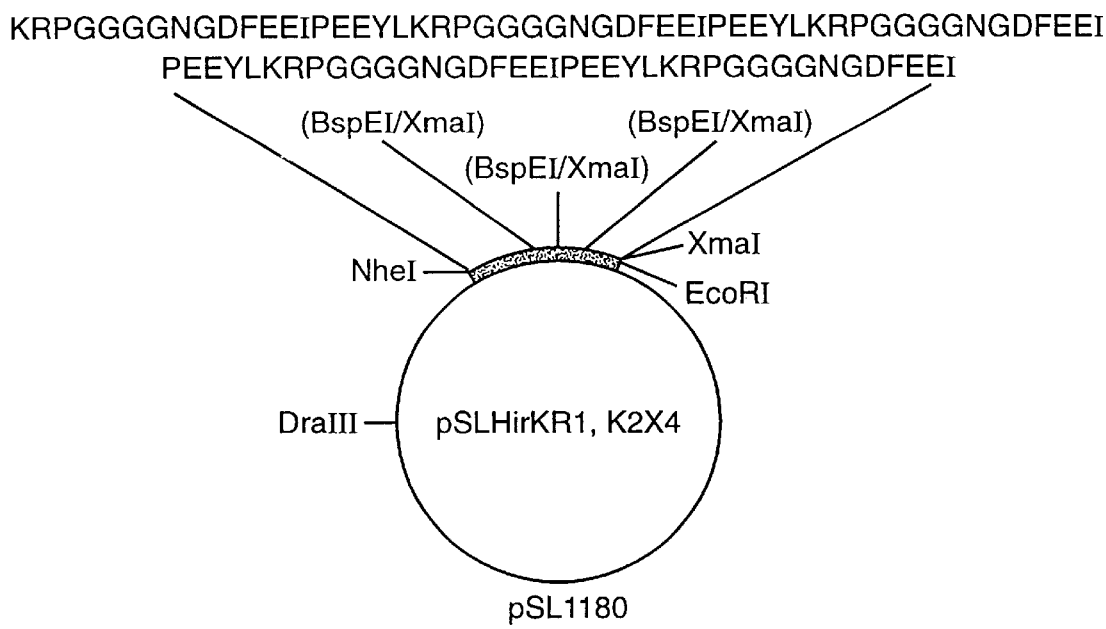
FIG._6A
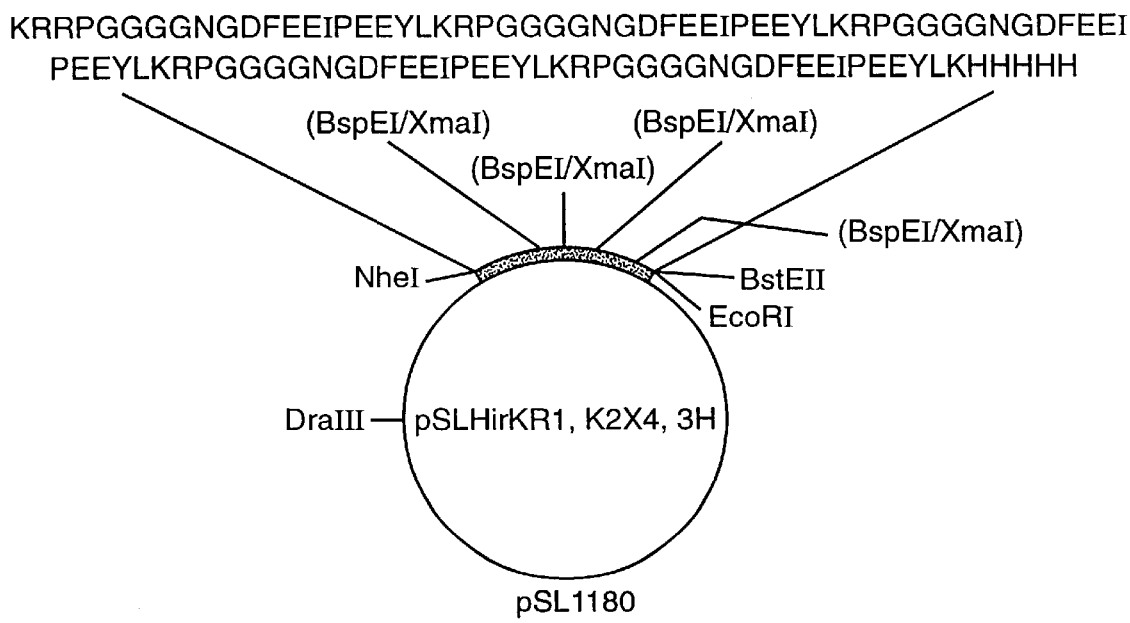
FIG._6B

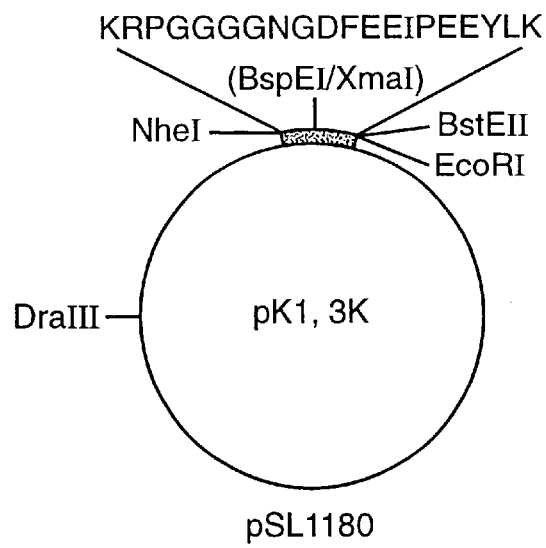
FIG._7
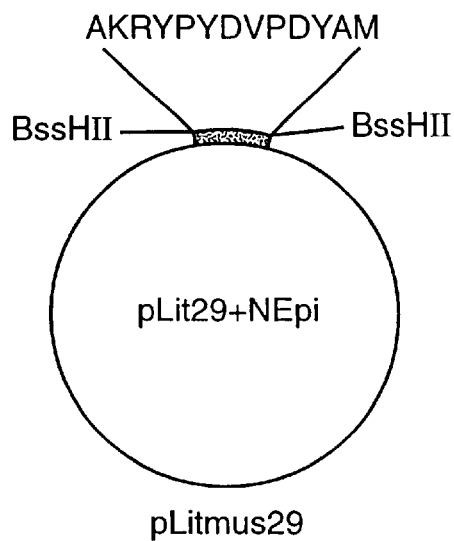
FIG._8A
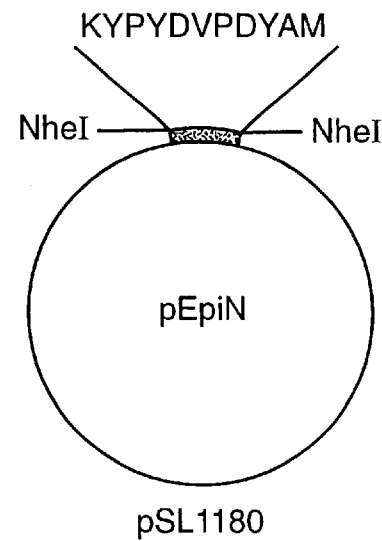
FIG._8B

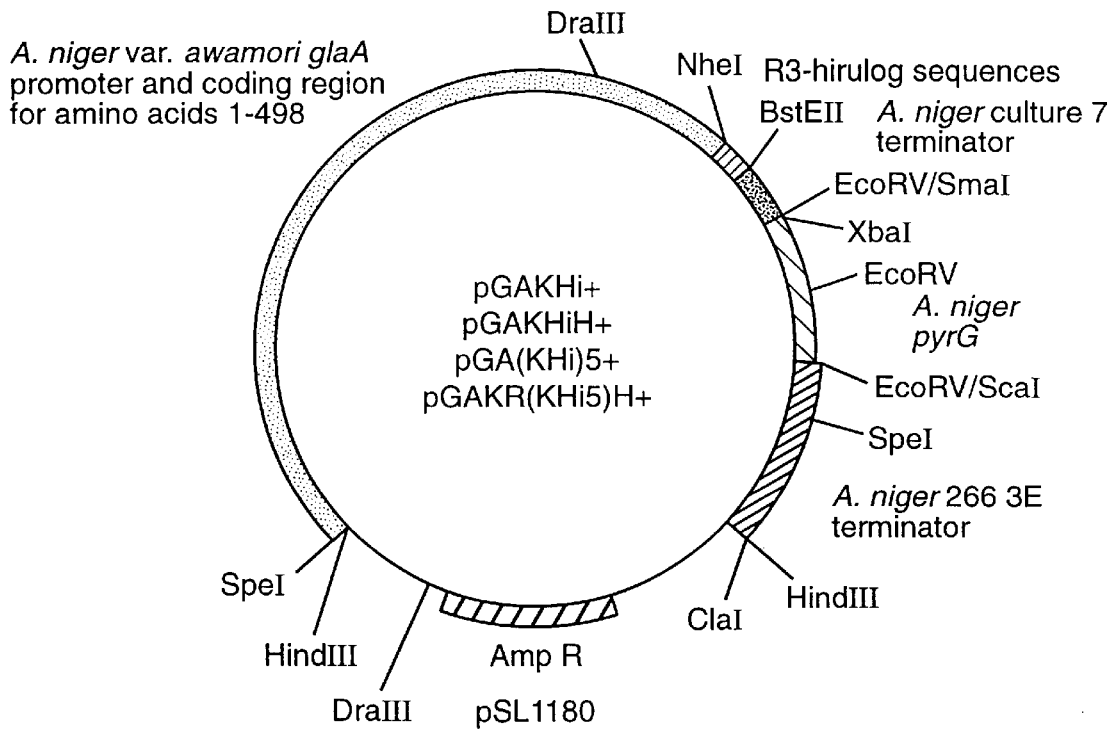
FIG._9
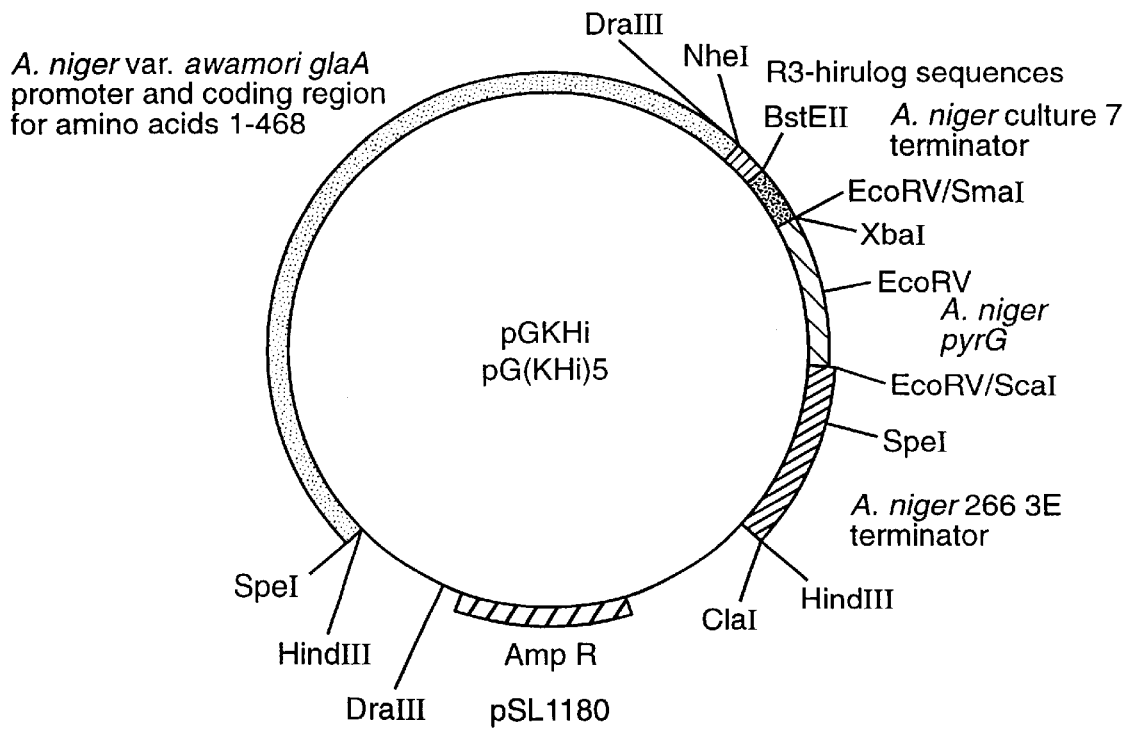
FIG._10

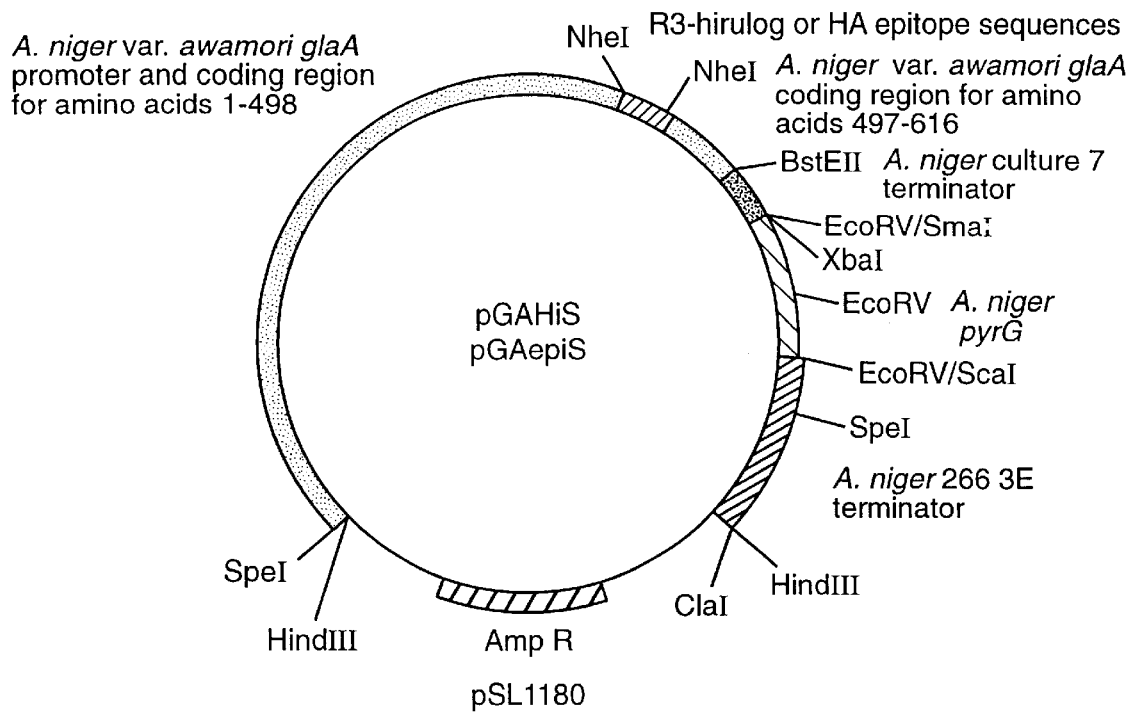
FIG._11
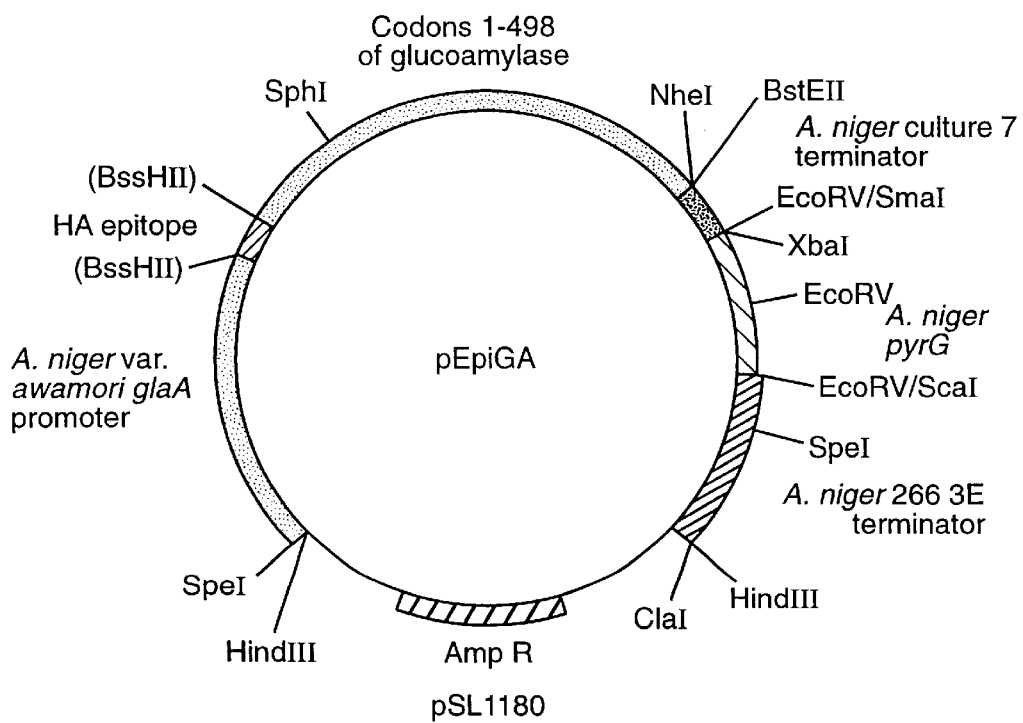
FIG._12

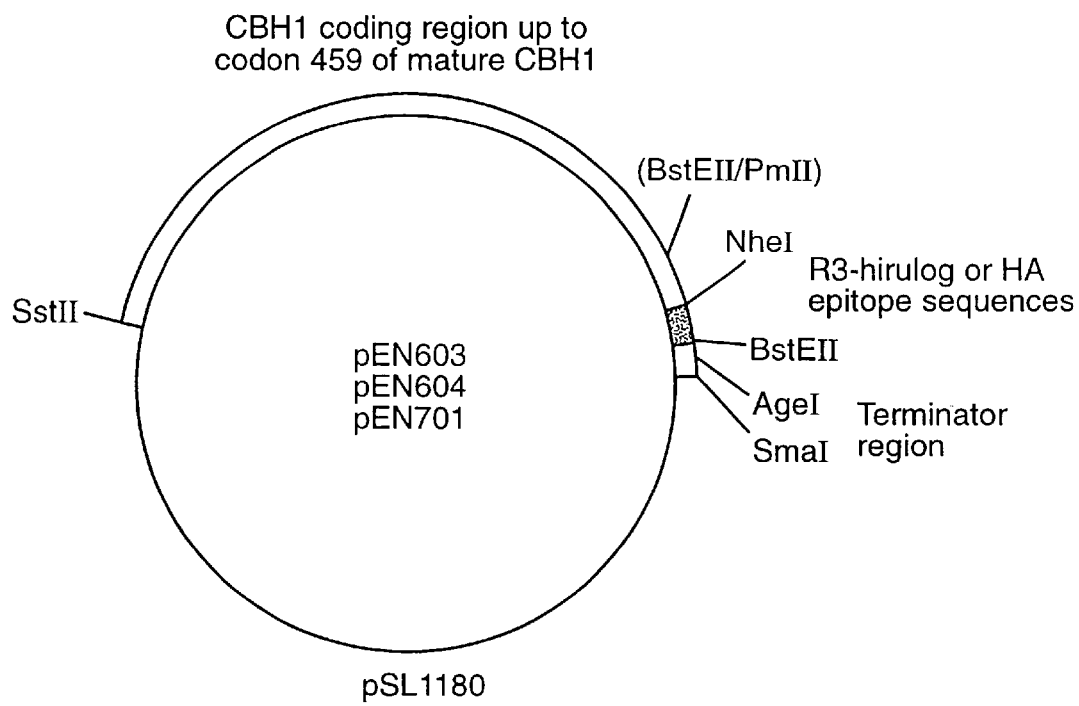
FIG._13
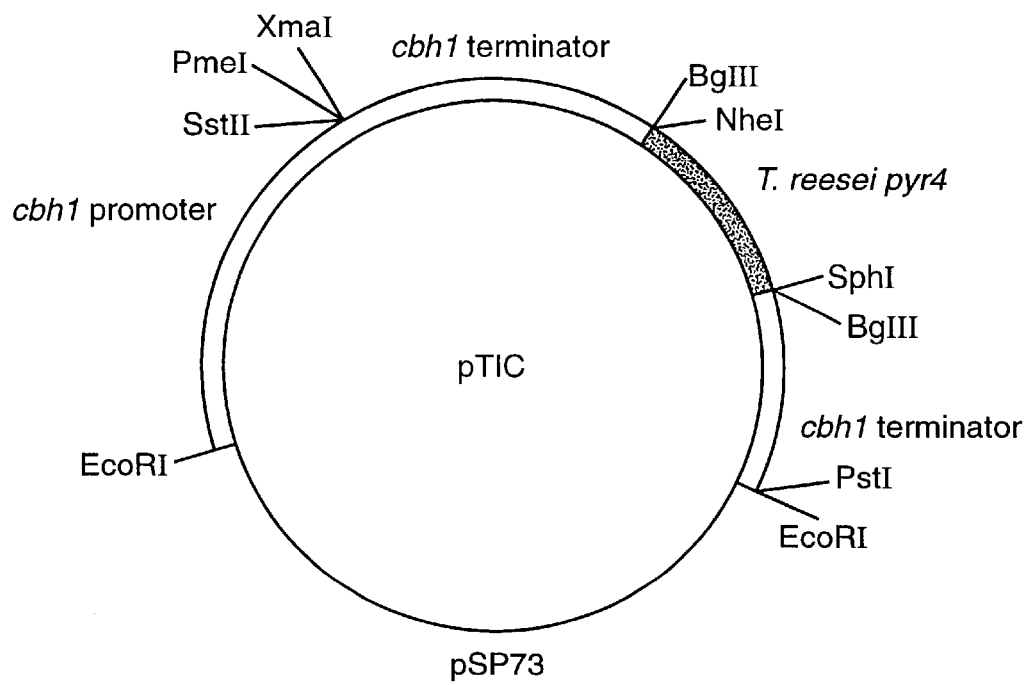
FIG._14

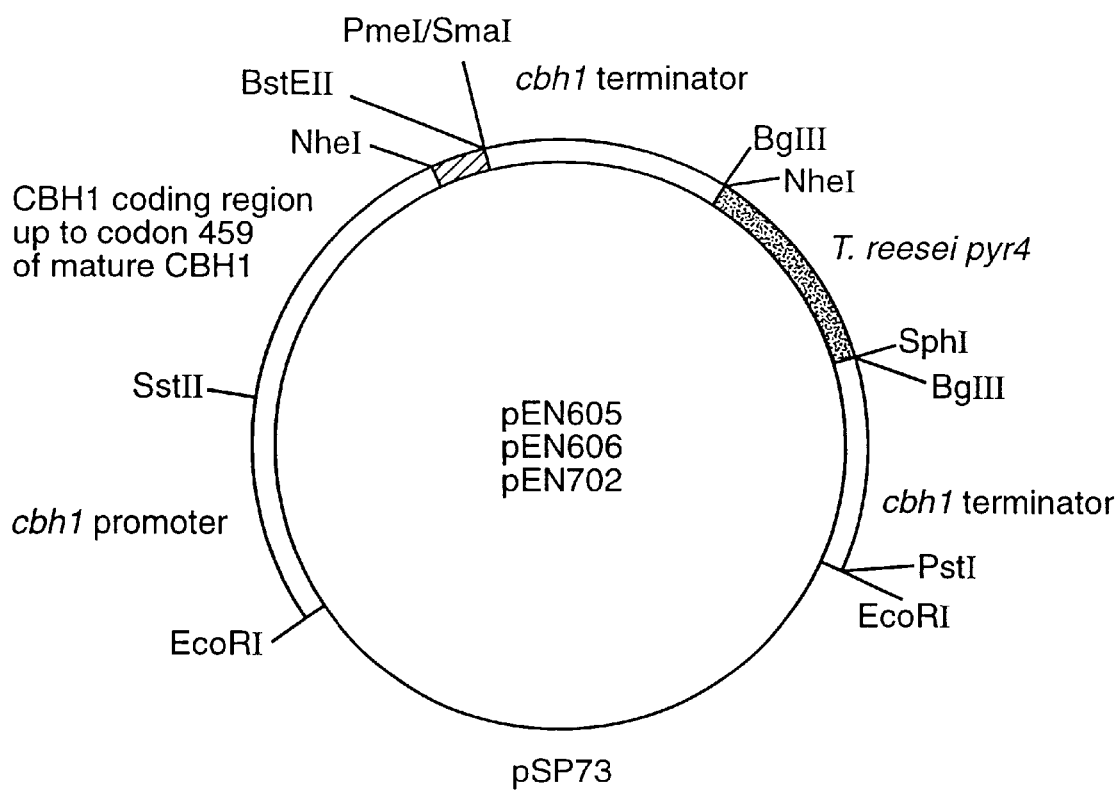
FIG._15

SEQUENCE LISTING

```
<160> NUMBER OF SEQ ID NOS: 44

<210> SEQ ID NO 1
<211> LENGTH: 14
<212> TYPE: PRT
<213> ORGANISM: Artificial Sequence
<220> FEATURE:
<223> OTHER INFORMATION: Synthetic.

<400> SEQUENCE: 1

Lys Arg Pro Gly Gly Gly Gly Asn Gly Asp Phe Glu Glu Ile
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic.

<400> SEQUENCE: 2

Lys Arg Arg Pro Gly Gly Gly Gly Asn Gly Asp Phe Glu Glu Ile
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: Synthetic.

<400> SEQUENCE: 3

Pro Glu Glu Tyr Leu Lys Arg Pro Gly Gly Gly Gly Asn Gly Asp Phe
1               5                   10                  15

Glu Glu Ile

<210> SEQ ID NO 4
<211> LENGTH: 5
<212> TYPE: PRT
```

```
<213> ORGANISM: Artificial Sequence
<220> FEATURE:
<223> OTHER INFORMATION: Synthetic.

<400> SEQUENCE: 4

Pro Glu Glu Tyr Leu
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic.

<400> SEQUENCE: 5

Pro Glu Glu Tyr Leu Lys His His His His
1               5                   10

<210> SEQ ID NO 6
<211> LENGTH: 19
<212> TYPE: PRT
<213> ORGANISM: Artificial Sequence
<220> FEATURE:
<223> OTHER INFORMATION: Synthetic.

<400> SEQUENCE: 6

Lys Arg Pro Gly Gly Gly Gly Asn Gly Asp Phe Glu Glu Ile Pro Glu
1               5                   10                  15

Glu Tyr Leu

<210> SEQ ID NO 7
<211> LENGTH: 25
<212> TYPE: PRT
<213> ORGANISM: Artificial Sequence
<220> FEATURE:
<223> OTHER INFORMATION: Synthetic.

<400> SEQUENCE: 7

Lys Arg Pro Gly Gly Gly Gly Asn Gly Asp Phe Glu Glu Ile Pro Glu
1               5                   10                  15

Glu Tyr Leu Lys His His His His His
            20                  25

<210> SEQ ID NO 8
<211> LENGTH: 38
<212> TYPE: PRT
<213> ORGANISM: Artificial Sequence
<220> FEATURE:
<223> OTHER INFORMATION: Synthetic.

<400> SEQUENCE: 8

Pro Glu Glu Tyr Leu Lys Arg Pro Gly Gly Gly Gly Asn Gly Asp Phe
1               5                   10                  15

Glu Glu Ile Pro Glu Glu Tyr Leu Lys Arg Pro Gly Gly Gly Gly Asn
            20                  25                  30

Gly Asp Phe Glu Glu Ile
            35

<210> SEQ ID NO 9
<211> LENGTH: 76
<212> TYPE: PRT
<213> ORGANISM: Artificial Sequence
<220> FEATURE:
<223> OTHER INFORMATION: Synthetic.
```

<400> SEQUENCE: 9

Pro Glu Glu Tyr Leu Lys Arg Pro Gly Gly Gly Asn Gly Asp Phe
1               5                   10                  15
Glu Glu Ile Pro Glu Glu Tyr Leu Lys Arg Pro Gly Gly Gly Asn
            20                  25                  30
Gly Asp Phe Glu Glu Ile Pro Glu Glu Tyr Leu Lys Arg Pro Gly
        35                  40                  45
Gly Gly Asn Gly Asp Phe Glu Glu Ile Pro Glu Glu Tyr Leu Lys Arg
    50                  55                  60
Pro Gly Gly Gly Asn Gly Asp Phe Glu Glu Ile
65                  70                  75

<210> SEQ ID NO 10
<211> LENGTH: 90
<212> TYPE: PRT
<213> ORGANISM: Artificial Sequence
<220> FEATURE:
<223> OTHER INFORMATION: Synthetic.

<400> SEQUENCE: 10

Lys Arg Pro Gly Gly Gly Gly Asn Gly Asp Phe Glu Glu Ile Pro Glu
1               5                   10                  15
Glu Tyr Leu Lys Arg Pro Gly Gly Gly Asn Gly Asp Phe Glu Glu
            20                  25                  30
Ile Pro Glu Glu Tyr Leu Lys Arg Pro Gly Gly Gly Asn Gly Asp
        35                  40                  45
Phe Glu Glu Ile Pro Glu Glu Tyr Leu Lys Arg Pro Gly Gly Gly Gly
    50                  55                  60
Asn Gly Asp Phe Glu Glu Ile Pro Glu Glu Tyr Leu Lys Arg Pro Gly
65                  70                  75                  80
Gly Gly Asn Gly Asp Phe Glu Glu Ile
                85                  90

<210> SEQ ID NO 11
<211> LENGTH: 95
<212> TYPE: PRT
<213> ORGANISM: Artificial Sequence
<220> FEATURE:
<223> OTHER INFORMATION: Synthetic.

<400> SEQUENCE: 11

Lys Arg Pro Gly Gly Gly Asn Gly Asp Phe Glu Glu Ile Pro Glu
1               5                   10                  15
Glu Tyr Leu Lys Arg Pro Gly Gly Gly Asn Gly Asp Phe Glu Glu
            20                  25                  30
Ile Pro Glu Glu Tyr Leu Lys Arg Pro Gly Gly Gly Asn Gly Asp
        35                  40                  45
Phe Glu Glu Ile Pro Glu Glu Tyr Leu Lys Arg Pro Gly Gly Gly Gly
    50                  55                  60
Asn Gly Asp Phe Glu Glu Ile Pro Glu Glu Tyr Leu Lys Arg Pro Gly
65                  70                  75                  80
Gly Gly Asn Gly Asp Phe Glu Glu Ile Pro Glu Glu Tyr Leu
                85                  90                  95

<210> SEQ ID NO 12
<211> LENGTH: 91
<212> TYPE: PRT
<213> ORGANISM: Artificial Sequence

```
<220> FEATURE:
<223> OTHER INFORMATION: Synthetic.

<400> SEQUENCE: 12

Lys Arg Arg Pro Gly Gly Gly Asn Gly Asp Phe Glu Glu Ile Pro
1               5                   10                  15

Glu Glu Tyr Leu Lys Arg Pro Gly Gly Gly Asn Gly Asp Phe Glu
            20                  25                  30

Glu Ile Pro Glu Glu Tyr Leu Lys Arg Pro Gly Gly Gly Asn Gly
        35                  40                  45

Asp Phe Glu Glu Ile Pro Glu Glu Tyr Leu Lys Arg Pro Gly Gly
    50                  55                  60

Gly Asn Gly Asp Phe Glu Glu Ile Pro Glu Glu Tyr Leu Lys Arg Pro
65                  70                  75                  80

Gly Gly Gly Gly Asn Gly Asp Phe Glu Glu Ile
                85                  90

<210> SEQ ID NO 13
<211> LENGTH: 102
<212> TYPE: PRT
<213> ORGANISM: Artificial Sequence
<220> FEATURE:
<223> OTHER INFORMATION: Synthetic.

<400> SEQUENCE: 13

Lys Arg Arg Pro Gly Gly Gly Asn Gly Asp Phe Glu Glu Ile Pro
1               5                   10                  15

Glu Glu Tyr Leu Lys Arg Pro Gly Gly Gly Asn Gly Asp Phe Glu
            20                  25                  30

Glu Ile Pro Glu Glu Tyr Leu Lys Arg Pro Gly Gly Gly Asn Gly
        35                  40                  45

Asp Phe Glu Glu Ile Pro Glu Glu Tyr Leu Lys Arg Pro Gly Gly
    50                  55                  60

Gly Asn Gly Asp Phe Glu Glu Ile Pro Glu Glu Tyr Leu Lys Arg Pro
65                  70                  75                  80

Gly Gly Gly Gly Asn Gly Asp Phe Glu Ile Pro Glu Glu Tyr Leu
                85                  90                  95

Lys His His His His His
            100

<210> SEQ ID NO 14
<211> LENGTH: 20
<212> TYPE: PRT
<213> ORGANISM: Artificial Sequence
<220> FEATURE:
<223> OTHER INFORMATION: Synthetic.

<400> SEQUENCE: 14

Lys Arg Pro Gly Gly Gly Gly Asn Gly Asp Phe Glu Ile Pro Glu
1               5                   10                  15

Glu Tyr Leu Lys
            20

<210> SEQ ID NO 15
<211> LENGTH: 13
<212> TYPE: PRT
<213> ORGANISM: Artificial Sequence
<220> FEATURE:
<223> OTHER INFORMATION: Synthetic.

<400> SEQUENCE: 15
```

Ala Lys Arg Tyr Pro Tyr Asp Val Pro Asp Tyr Ala Met
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic.

<400> SEQUENCE: 16

Lys Tyr Pro Tyr Asp Val Pro Asp Tyr Ala Met
1               5                   10

<210> SEQ ID NO 17
<211> LENGTH: 18
<212> TYPE: PRT
<213> ORGANISM: Artificial Sequence
<220> FEATURE:
<223> OTHER INFORMATION: R3-hirulog.

<400> SEQUENCE: 17

Arg Pro Gly Gly Gly Gly Asn Gly Asp Phe Glu Glu Ile Pro Glu Glu
1               5                   10                  15

Tyr Leu

<210> SEQ ID NO 18
<211> LENGTH: 95
<212> TYPE: PRT
<213> ORGANISM: Artificial Sequence
<220> FEATURE:
<223> OTHER INFORMATION: R3-hirulog oligonucleotide.

<400> SEQUENCE: 18

Lys Arg Pro Gly Gly Gly Gly Asn Gly Asp Phe Glu Glu Ile Pro Glu
1               5                   10                  15

Glu Tyr Leu Lys Arg Pro Gly Gly Gly Gly Asn Gly Asp Phe Glu Glu
                20                  25                  30

Ile Pro Glu Glu Tyr Leu Lys Arg Pro Gly Gly Gly Gly Asn Gly Asp
        35                  40                  45

Phe Glu Glu Ile Pro Glu Glu Tyr Leu Lys Arg Pro Gly Gly Gly Gly
    50                  55                  60

Asn Gly Asp Phe Glu Glu Ile Pro Glu Glu Tyr Leu Lys Arg Pro Gly
65                  70                  75                  80

Gly Gly Asn Gly Asp Phe Glu Glu Ile Pro Glu Glu Tyr Leu
                85                  90                  95

<210> SEQ ID NO 19
<211> LENGTH: 100
<212> TYPE: PRT
<213> ORGANISM: Artificial Sequence
<220> FEATURE:
<223> OTHER INFORMATION: R3-hirulog oligonucleotide.

<400> SEQUENCE: 19

Lys Arg Arg Pro Gly Gly Gly Gly Asn Gly Asp Phe Glu Glu Ile Pro
1               5                   10                  15

Glu Glu Tyr Leu Lys Arg Arg Pro Gly Gly Gly Gly Asn Gly Asp Phe
                20                  25                  30

Glu Glu Ile Pro Glu Glu Tyr Leu Lys Arg Arg Pro Gly Gly Gly Gly
        35                  40                  45

```
Asn Gly Asp Phe Glu Glu Ile Pro Glu Tyr Leu Lys Arg Arg Pro
 50                  55                  60

Gly Gly Gly Gly Asn Gly Asp Phe Glu Ile Pro Glu Glu Tyr Leu
 65                  70                  75                  80

Lys Arg Arg Pro Gly Gly Gly Asn Gly Asp Phe Glu Ile Pro
                 85                  90                  95

Glu Glu Tyr Leu
        100
```

```
<210> SEQ ID NO 20
<211> LENGTH: 47
<212> TYPE: DNA
<213> ORGANISM: Artificial Sequence
<220> FEATURE:
<223> OTHER INFORMATION: Synthetic.

<400> SEQUENCE: 20
ctagcaagcg ccccggcggc ggcggcaacg gcgacttcga ggagatc          47

<210> SEQ ID NO 21
<211> LENGTH: 47
<212> TYPE: DNA
<213> ORGANISM: Artificial Sequence
<220> FEATURE:
<223> OTHER INFORMATION: Synthetic.

<400> SEQUENCE: 21
ccgggatctc ctcgaagtcg ccgttgccgc cgccgccggg gcgcttg          47

<210> SEQ ID NO 22
<211> LENGTH: 49
<212> TYPE: DNA
<213> ORGANISM: Artificial Sequence
<220> FEATURE:
<223> OTHER INFORMATION: Synthetic.

<400> SEQUENCE: 22
ctagcaagcg ccgccccggc ggcggcggca acggcacttc gaggagatc          49

<210> SEQ ID NO 23
<211> LENGTH: 50
<212> TYPE: DNA
<213> ORGANISM: Artificial Sequence
<220> FEATURE:
<223> OTHER INFORMATION: Synthetic.

<400> SEQUENCE: 23
ccgggatctc ctcgaagtcg ccgttgccgc cgccgccggg gcggcgcttg          50

<210> SEQ ID NO 24
<211> LENGTH: 57
<212> TYPE: DNA
<213> ORGANISM: Artificial Sequence
<220> FEATURE:
<223> OTHER INFORMATION: Synthetic.

<400> SEQUENCE: 24
ccggaggagt acctgaagcg ccccggcggc ggcggcaacg gcgacttcga ggagatc          57

<210> SEQ ID NO 25
<211> LENGTH: 57
<212> TYPE: DNA
<213> ORGANISM: Artificial Sequence
<220> FEATURE:
<223> OTHER INFORMATION: Synthetic.
```

```
<400> SEQUENCE: 25
ccgggatctc tcgaagtcg ccgttgccgc cgccgccggg gcgcttcagg tactcct        57

<210> SEQ ID NO 26
<211> LENGTH: 25
<212> TYPE: DNA
<213> ORGANISM: Artificial Sequence
<220> FEATURE:
<223> OTHER INFORMATION: Synthetic.

<400> SEQUENCE: 26
ccggaggagt acctgtaggt gaccg                                           25

<210> SEQ ID NO 27
<211> LENGTH: 25
<212> TYPE: DNA
<213> ORGANISM: Artificial Sequence
<220> FEATURE:
<223> OTHER INFORMATION: Synthetic.

<400> SEQUENCE: 27
aattcggtca cctacaggta ctcct                                           25

<210> SEQ ID NO 28
<211> LENGTH: 43
<212> TYPE: DNA
<213> ORGANISM: Artificial Sequence
<220> FEATURE:
<223> OTHER INFORMATION: Synthetic.

<400> SEQUENCE: 28
ccggaggagt acctgaagca ccaccaccac cactaggtga ccg                       43

<210> SEQ ID NO 29
<211> LENGTH: 43
<212> TYPE: DNA
<213> ORGANISM: Artificial Sequence
<220> FEATURE:
<223> OTHER INFORMATION: Synthetic.

<400> SEQUENCE: 29
aattcggtca cctagtggtg gtggtggtgc ttcaggtact cct                       43

<210> SEQ ID NO 30
<211> LENGTH: 25
<212> TYPE: DNA
<213> ORGANISM: Artificial Sequence
<220> FEATURE:
<223> OTHER INFORMATION: Synthetic.

<400> SEQUENCE: 30
ccggaggagt acctgaaggc tagcg                                           25

<210> SEQ ID NO 31
<211> LENGTH: 25
<212> TYPE: DNA
<213> ORGANISM: Artificial Sequence
<220> FEATURE:
<223> OTHER INFORMATION: Synthetic.

<400> SEQUENCE: 31
aattcgctag ccttcaggta ctcct                                           25

<210> SEQ ID NO 32
```

```
<211> LENGTH: 9
<212> TYPE: PRT
<213> ORGANISM: Artificial Sequence
<220> FEATURE:
<223> OTHER INFORMATION: Synthetic.

<400> SEQUENCE: 32

Tyr Pro Tyr Asp Val Pro Asp Tyr Ala
1               5

<210> SEQ ID NO 33
<211> LENGTH: 39
<212> TYPE: DNA
<213> ORGANISM: Artificial Sequence
<220> FEATURE:
<223> OTHER INFORMATION: Synthetic.

<400> SEQUENCE: 33
ctagcaagta cccctacgat gtgcccgact acgctatgg                              39

<210> SEQ ID NO 34
<211> LENGTH: 39
<212> TYPE: DNA
<213> ORGANISM: Artificial Sequence
<220> FEATURE:
<223> OTHER INFORMATION: Synthetic.

<400> SEQUENCE: 34
ctagccatag cgtagtcggg cacatcgtag gggtacttg                              39

<210> SEQ ID NO 35
<211> LENGTH: 42
<212> TYPE: DNA
<213> ORGANISM: Artificial Sequence
<220> FEATURE:
<223> OTHER INFORMATION: Synthetic.

<400> SEQUENCE: 35
cgcgctaagc gctaccccta cgatgtgccc gactacgcta tg                         42

<210> SEQ ID NO 36
<211> LENGTH: 42
<212> TYPE: DNA
<213> ORGANISM: Artificial Sequence
<220> FEATURE:
<223> OTHER INFORMATION: Synthetic.

<400> SEQUENCE: 36
cgcgcatagc gtagtcgggc acatcgtagg ggtagcgctt ag                         42

<210> SEQ ID NO 37
<211> LENGTH: 11
<212> TYPE: DNA
<213> ORGANISM: Artificial Sequence
<220> FEATURE:
<223> OTHER INFORMATION: Synthetic.

<400> SEQUENCE: 37
ctagcaagta g                                                           11

<210> SEQ ID NO 38
<211> LENGTH: 12
<212> TYPE: DNA
<213> ORGANISM: Artificial Sequence
<220> FEATURE:
<223> OTHER INFORMATION: Synthetic.
```

```
<400> SEQUENCE: 38
gtcacctact tg                                                        12

<210> SEQ ID NO 39
<211> LENGTH: 5
<212> TYPE: PRT
<213> ORGANISM: Artificial Sequence
<220> FEATURE:
<223> OTHER INFORMATION: Synthetic.

<400> SEQUENCE: 39

Gly Gly Gly Gly Asn
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic.

<400> SEQUENCE: 40

Arg Pro Gly Gly Gly Asn
        1               5

<210> SEQ ID NO 41
<211> LENGTH: 11
<212> TYPE: DNA
<213> ORGANISM: Artificial Sequence
<220> FEATURE:
<223> OTHER INFORMATION: Synthetic.

<400> SEQUENCE: 41
gtggccgagt g                                                         11

<210> SEQ ID NO 42
<211> LENGTH: 18
<212> TYPE: DNA
<213> ORGANISM: Artificial Sequence
<220> FEATURE:
<223> OTHER INFORMATION: Synthetic.

<400> SEQUENCE: 42
ctagcactcg gccacgag                                                  18

<210> SEQ ID NO 43
<211> LENGTH: 37
<212> TYPE: DNA
<213> ORGANISM: Artificial Sequence
<220> FEATURE:
<223> OTHER INFORMATION: primer sequence.

<400> SEQUENCE: 43
cttcacacgt gactttctcc aacatcaagt tcggacc                             37

<210> SEQ ID NO 44
<211> LENGTH: 53
<212> TYPE: DNA
<213> ORGANISM: Artificial Sequence
<220> FEATURE:
<223> OTHER INFORMATION: primer sequence.

<400> SEQUENCE: 44
aatctaccgg tggtcaccgc gcttgctagc tccgggagag cttccagtgg tag           53
```

US 6,590,078 B2

DNA SEQUENCES, VECTORS, AND FUSION POLYPEPTIDES FOR SECRETION OF POLYPEPTIDES IN FILAMENTOUS FUNGI

This is a divisional of application Ser. No. 08/785,668 filed Jan. 17, 1997, Now U.S. Pat. No. 6,265,204, incorporated herein in its entirety.

FIELD OF THE INVENTION

The present invention is directed to increased secretion of desired polypeptides from filamentous fungi. The invention discloses fusion nucleic acids, vectors, fusion polypeptides, and processes for obtaining the desired polypeptide.

BACKGROUND OF THE INVENTION

Production of fusion polypeptides has been reported in a number of organisms, including E. coli, yeast, and filamentous fungi. For example, bovine chymosin and porcine pancreatic prophospholipase $A_2$ have both been produced in A. niger or A. niger var. awamori as fusions to full-length GAI (U.S. Ser. No. 08/318,494; Ward et al., Bio/technology 8: 435–440,1990; Roberts et al.,Gene 122: 155–161, 1992). Human interleukin 6 (hIL6) has been produced in A. nidulans as a fusion to full-length A. niger GAI (Contreras et al., Biotechnology 9: 378–381, 1991). Hen egg white lysozyme (Jeenes et al., FEMS Microbiol. Lett. 107: 267–272, 1993) and human lactoferrin (Ward et al., Bio/technology 13: 498–503, 1995) have been produced in A. niger as fusions to residues 1–498 of glucoamylase and hIL6 has been produced in A. niger as a fusion to glucoamylase residues 1–514 (Broekhuijsen et al., J. Biotechnol. 31: 135–145, 1993). In some of the above experiments (Contreras et al., 1991; Broekhuijsen et al., 1993; Ward et al., 1995) a KEX2 protease recognition site (Lys, Arg) has been inserted between glucoamylase and the desired polypeptide to allow in vivo release of the desired polypeptide from the fusion protein as a result of the action of a native Aspergillus KEX2-like protease.

Additionally, bovine chymosin has been produced in A. niger as a fusion with full-length native alpha-amylase (Korman et al., Curr. Genet. 17: 203–212, 1990) and in A. oryzae as a fusion with truncated forms of A. oryzae glucoamylase (either residues 1–603 or 1–511; Tsuchiya et al., Biosci. Biotech. Biochem. 58: 895–899, 1994).

A small protein (epidermal growth hormone; 53 amino acids) has been produced in Aspergillus as a tandem fusion of three copies of the protein (U.S. Pat. No. 5,218,093). The trimer of EGF was secreted as a result of the inclusion of an N-terminal secretion signal sequence. However, the EGF molecules were not additionally fused to a protein efficiently secreted by filamentous fungi and no method for subsequent separation of monomeric EGF proteins was provided.

The glaA gene encodes glucoamylase which is highly expressed in many strains of Aspergillus niger and Aspergillus awamori. The promoter and secretion signal sequence of the gene have been used to express heterologous genes in Aspergillus including bovine chymosin in Aspergillus nidulans and A. awamori as previously described (Gwynne, D. et al. (1987) Bio/Technology 5, 713–719 and EPO Publication No. 0 215 594). In the latter experiments, a variety of constructs were made, incorporating prochymosin cDNA, either the glucoamylase or the chymosin secretion signal and, in one case, the first 11 codons of mature glucoamylase. Maximum yields of secreted chymosin obtained from A. awamori were below 15 mg/l in 50 ml shake flask cultures and were obtained using the chymosin signal sequence encoded by pGRG3. These previous studies indicated that integrated plasmid copy number did not correlate with chymosin yields, abundant polyadenylated chymosin mRNA was produced, and intracellular levels of chymosin were high in some transformants regardless of the source of secretion signal. It was inferred that transcription was not a limiting factor in chymosin production but that secretion may have been inefficient. It was also evident that the addition of a small amino terminal segment (11 amino acids) of glucoamylase to the propeptide of prochymosin did not prevent activation to mature chymosin. The amount of extracellular chymosin obtained with the first eleven codons of glucoamylase, however, was substantially less than that obtained when the glucoamylase signal was used alone. Subsequently, it was demonstrated that chymosin production could be greatly increased when a fusion protein consisting of full-length glucoamylase and prochymosin was produced (U.S. Ser. No. 08/318,494; Ward et al. Bio/technology 8: 435–440, 1990).

Aspergillus niger and Aspergillus niger var. awamori (A. awamori) glucoamylases have identical amino acid sequences. The glucoamylase is initially synthesized as preproglucoamylase. The pre and pro regions are removed during the secretion process so that mature glucoamylase is released to the external medium. Two forms of mature glucoamylase are recognized in culture supernatants: GAI is the full-length form (amino acid residues 1–616) and GAII is a natural proteolytic fragment comprising amino acid residues 1–512. GAI is known to fold as two separate domains joined by an extended linker region. The two domains are the 471 residue catalytic domain (amino acids 1–471) and the 108 residue starch binding domain (amino acids 509–616), the linker region being 36 residues in length (amino acids 472–508). GAII lacks the starch binding domain. These details of glucoamylase structure are reviewed by Libby et al. (Protein Engineering 7: 1109–1114, 1994) and are shown diagrammatically in FIG. 1.

Trichoderma reesei produces several cellulase enzymes, including cellobiohydrolase I (CBHI), which are folded into two separate domains (catalytic and binding domains) separated by an extended linker region. Foreign polypeptides have been secreted in T. reesei as fusions with the catalytic domain plus linker region of CBHI (Nyyssonen et al., Bio/technology 11: 591–595, 1993).

SUMMARY OF THE INVENTION

An object of the invention herein is to provide for the expression and secretion of desired polypeptides by and from filamentous fungi including fusion nucleic acids, expression vectors containing such fusion nucleic acids, transformed filamentous fungi, fusion polypeptides and processes for expressing and secreting high levels of such desired polypeptides.

In accordance with the above objects, the invention provides fusion nucleic acids encoding a fusion polypeptide comprising, from a 5' end of the fusion nucleic acid, first, second, third and fourth nucleic acids. The first nucleic acid encodes a signal polypeptide functional as a secretory sequence in a first filamentous fungus. The second nucleic acid encodes a secreted polypeptide or functional portion normally secreted from a filamentous fungus. The third nucleic acid encodes a cleavable linker and the fourth nucleic acid comprises two or more nucleic acids each encoding desired polypeptides.

Further provided are fusion nucleic acids wherein the fourth nucleic acid further comprises at least one nucleic acid encoding a cleavable linker. The nucleic acids encoding said desired polypeptides are separated by the nucleic acid encoding the cleavable linker.

In another aspect, the invention provides a fusion nucleic acid encoding a fusion polypeptide comprising, from a 5' end of the fusion nucleic acid, first, fifth, third and second nucleic acids. The fifth nucleic acid comprises at least one nucleic acid encoding a desired polypeptide.

In a further aspect the invention provides a fusion polypeptide comprising a first nucleic acid, a second nucleic acid, and an insertion nucleic acid. The insertion nucleic acid comprises a fifth nucleic acid flanked by third nucleic acids.

Also provided are expression vectors for transforming a host filamentous fungus comprising nucleic acids encoding regulatory sequences functionally recognized by said host filamentous fungus including promoter and transcription and translation initiation sequences operably linked to the 5' end of the fusion nucleic acids described herein.

Although cleavage of the fusion polypeptide to release the desired polypeptide will often be useful, it is not necessary. In those cases in which the desired polypeptide retains its functionality when it is part of the fusion, polypeptide cleavage may not be required or desirable. For this reason, said third amino acid sequence comprising the cleavable linker may be considered optional.

Also provided are filamentous fungi containing a fusion nucleic acid described herein.

Additionally provided are fusion polypeptides comprising, from the amino-to caboxy-terminus, first, second, third and fourth amino acid sequences. The first amino acid sequence comprises a signal polypeptide functional as a secretory sequence in a filamentous fungus. The second amino acid sequence comprises a secreted polypeptide or functional portion normally secreted from a filamentous fungus. The third amino acid sequence comprises a cleavable linker and the fourth amino acid sequence comprises at least two desired polypeptides.

Further provided are fusion polypeptides comprising, from the amino-to caboxy-terminus, first, fifth, third and second amino acids. The fifth polypeptide comprises at least one desired polypeptide.

Also provided are fusion polypeptides comprising a first amino acid sequence, a second amino acid sequence, and an insertion amino acid sequence. The insertion amino acid sequence comprises a fifth amino acid sequence flanked by third amino acid sequences, and is inserted into the second amino acid sequence.

Additionally provided are processes for producing a desired polypeptide comprising transforming a host filamentous fungus with an expression vector containing a fusion nucleic acid described herein under conditions which permit expression of the fusion nucleic acid to cause the secretion of the desired polypeptide encoded by the fusion nucleic acid.

BRIEF DESCRIPTION OF THE DRAWINGS

FIGS. 1A and 1B depict the structure of *A. niger* glucoamylases. FIG. 1A depicts GAI, and FIG. 1B depicts GAII.

FIGS. 2A, 2B, 2C, 2D, and 2E (SEQ ID NOS: 1–5) depict five plasmids containing synthetic DNA with the important restriction sites and amino acids encoded by the oligonucleotides.

FIGS. 3A and 3B (SEQ ID NOS: 6–7) depict two plasmids containing synthetic DNA with the important restriction sites and amino acids encoded by the oligonucleotides.

FIGS. 4A and 4B (SEQ ID NOS: 8–9) depict two plasmids containing synthetic DNA with the important restriction sites and amino acids encoded by the oligonucleotides.

FIGS. 5A and 5B (SEQ ID NOS: 10–11) depict two plasmids containing synthetic DNA with the important restriction sites and amino acids encoded by the oligonucleotides.

FIGS. 6A and 6B (SEQ ID NOS: 12–13) depict two plasmids containing synthetic DNA with the important restriction sites and amino acids encoded by the oligonucleotides.

FIG. 7 (SEQ ID NO: 14) depicts a plasmid containing synthetic DNA with the important restriction sites and amino acids encoded by the oligonucleotides.

FIGS. 8A and 8B (SEQ ID NOS: 15–16) depict two plasmids containing synthetic DNA with the important restriction sites and amino acids encoded by the oligonucleotides.

FIG. 9 depicts the pGA plasmids containing the *A. niger* var. *awamori* glaA promoter and coding region for amino acids 1–498 of mature glucoamylase and sequences encoding desired polypeptides positioned at the 3' end.

FIG. 10 depicts the pG plasmids containing the *A. niger* var. *awamori* glaA promoter and coding region for amino acids 1–468 of mature glucoamylase and sequences encoding desired polypeptides positioned at the 3' end.

FIG. 11 depicts the pGAXS plasmids containing the *A. niger* var. *awamori* glaA promoter and coding region for amino acids 1–616 of mature glucoamylase and with sequences encoding desired polypeptides inserted after the codon for amino acid 498 of mature glucoamylase.

FIG. 12 depicts pEpiGA containing the *A. niger* var. *awamori* glaA promoter and epitope positioned at the 5' end of the coding region for amino acids 1–498 of mature glucoamylase.

FIG. 13 depicts pEN603, pEN604 and pEN701 containing the coding region for *Trichoderma longibrachiatum* CBHI up to codon 459 of mature CBHI and sequences encoding desired polypeptides positioned at the 3' end.

FIG. 14 depicts pTIC, a *Trichoderma longibrachiatum* expression vector containing the promotor and terminator regions of the cbhl gene and the pyr4 gene as a delectable marker.

FIG. 15 depicts pEN605, pEN606, pEN702 which are vectors designed for expression in *Trichoderma longibrachiatum* of fusion proteins containing CBHI up to amino acid 459 with desired polypeptides fused at the carboxyl terminus.

DETAILED DESCRIPTION

It was previously discovered that desired polypeptides can be expressed and secreted at levels higher than that previously obtained by fusing the desired polypeptide with a functional polypeptide which is normally secreted from a filamentous fungus. It has been previously shown that heterologous polypeptides such as bovine chymosin, glucoamylase and carboxyl (=aspartyl) protease from filamentous fungi could be expressed and secreted from Aspergillus species as described in U.S. Pat. No. 5,364,770, EPO Publication No. 0 215 594, and WO 90/15860, each of which are expressly incorporated herein by reference.

In a preferred embodiment, the present invention provides improved fusion nucleic acids comprising first, second, third and fourth nucleic acids. The first nucleic acid encodes a signal polypeptide functional as a secretory sequence in a first filamentous fungus. The second nucleic acid encodes a secreted polypeptide or functional portion of a secreted polypeptide that is normally secreted from a filamentous fungus. The third nucleic acid encodes a cleavable linker, send the fourth nucleic acid encodes at least two desired polypeptides.

As used herein, a "fusion nucleic acid" comprises a number of nucleic acids operably linked together, as described herein. By "nucleic acid" herein is meant at least two nucleotides covalently linked together. The nucleic acid may be DNA, both genomic and cDNA, or RNA, or a hybrid of RNA and DNA. Preferred nucleic acid is DNA.

The "first nucleic acid" encodes a signal polypeptide functional as a secretory sequence in a first filamentous fungus. Such signal sequences include those from glucoamylase, α-amylase and aspartyl proteases from *Aspergillus awamori, Aspergillus niger, Aspergillus oryzae*, signal sequences from cellobiohydrolase I, cellobiohydrolase II, endoglucanase I, endoglucanase II, endoglucanase III from Trichoderma, signal sequences from glucoamylase from Neurospora and Humicola as well as signal sequences from eukaryotes including the signal sequence from bovine chymosin, human tissue plasminogen activator, human interferon and synthetic consensus eukaryotic signal sequences such as that described by Gwynne et al. (1987) supra. Particularly preferred signal sequences are those derived from polypeptides secreted by the expression host used to express and secrete the fusion polypeptide. For example, the signal sequence from glucoamylase from *Aspergillus awamori* is preferred when expressing and secreting a fusion polypeptide from *Aspergillus awamori*.

As used herein, first amino acid sequences correspond to secretory sequences which are functional in a filamentous fungus. Such amino acid sequences are encoded by first nucleic acids as defined.

As used herein, "second nucleic acids" encode all or part of "secreted polypeptides" normally expressed from filamentous fungi. Such secreted polypeptides include glucoamylase, α-amylase and aspartyl proteases from *Aspergillus niger, Aspergillus niger* var. *awamori*, and *Aspergillus oryzae*, cellobiohydrolase I, cellobiohydrolase II, endoglucanase I and endoglucanase III from Trichoderma and glucoamylase from Nuerospora species and Humicola species. As with the first nucleic acids, preferred secreted polypeptides are those which are naturally secreted by the filamentous fungal expression host. Thus, for example when using *Aspergillus niger* var. *awamori*, preferred secreted polypeptides are glucoamylase and α-amylase from *Aspergillus niger* var. *awamori*, most preferably glucoamylase.

As indicated, all or part of the mature sequence of the secreted polypeptide is used in the construction of the fusion DNA sequences. In one embodiment, full length secreted polypeptides are used. However, functional portions of the secreted polypeptide may be employed. As used herein a "portion" of a secreted polypeptide may be defined in one of two ways. Preferably, a portion of a secreted polypeptide is defined functionally as that portion of a secreted polypeptide which when combined with the other components of the fusion polypeptide defined herein results in increased secretion of the desired polypeptide as compared to the level of desired polypeptide secreted when an expression vector is used which does not utilize the secreted polypeptide. Thus, the secretion level of a fusion DNA sequence encoding first, second, third and fourth amino acid sequences (the second DNA sequence containing all or a portion of a secreted polypeptide) is compared to the secretion level for a second fusion polypeptide containing only first, third and fourth amino acid sequences (i.e., without a secreted polypeptide or a portion thereof). Those amino acid sequences from the secreted polypeptide, and DNA sequences encoding such amino acids, which are capable of producing increased secretion as compared to the second fusion polypeptide comprise the "portion" of the secreted polypeptide as defined herein.

A "functional portion of a secreted polypeptide" or grammatical equivalents may also mean a truncated secreted polypeptide that retains its ability to fold into a normal, albeit truncated, configuration. For example, in the case of bovine chymosin production by *A. niger* var. *awamori* it has been shown that fusion of prochymosin following the 11th amino acid of mature glucoamylase provided no benefit compared to production of preprochymosin (U.S. Pat. No 5,364,770). In U.S. Ser. No. 08/318,494, it was shown that fusion of prochymosin onto the C-terminus of preproglucoamylase up to the 297th amino acid of mature glucoamylase plus a repeat of amino acids 1–11 of mature glucoamylase yielded no secreted chymosin in *A. niger* var. *awamori*. In the latter case it is unlikely that the portion (approximately 63%) of the glucoamylase catalytic domain present in the fusion protein was able to fold correctly so that an aberrant, misfolded and/or unstable fusion protein may have been produced which could not be secreted by the cell. The inability of the partial catalytic domain to fold correctly may have interfered with the folding of the attached chymosin. Thus, it is likely that sufficient residues of a domain of the naturally secreted polypeptide must be present to allow it to fold in its normal configuration independently of the desired polypeptide to which it is attached. Evans et al. (Gene 91: 131–134, 1990) showed that a form of *A. niger* glucoamylase truncated at its C-terminus back to amino acid 460 in the catalytic domain was not efficiently secreted by yeast. However, the relevance of this to secretion in Aspergillus is not known.

In most cases, the portion of the secreted polypeptide will be both correctly folded and result in increased secretion as compared to its absence.

Similarly, in most cases, the truncation of the secreted polypeptide means that the functional portion retains a biological function. In a preferred embodiment, the catalytic domain of a secreted polypeptide is used, although other functional domains may be used, for example, the substrate binding domains. In the case of *Aspergillus niger* and *Aspergillus niger* var. *awamori* glucoamylase, preferred functional portions retain the catalytic domain of the enzyme, and include amino acids 1–471. Additionally preferred embodiments utilize the catalytic domain and all or part of the linker region. Alternatively, the starch binding domain of glucoamylase may be used, which comprises amino acids 509–616 of *Aspergillus niger* and *Aspergillus niger* var. *awamori* glucoamylase.

In a preferred embodiment, the functional portion of the secreted polypeptide includes a linker region. The salient features of a linker region are that it forms an extended, semi-rigid spacer between independently folded domains. A linker region between the desired polypeptide and the functional domain of the naturally secreted fungal polypeptide may be beneficial in allowing the two polypeptides to fold independently. As is known in the art and discussed above, a number of secreted polypeptides are known to contain linkers, including hydrolases such as bacterial and fungal cellulases and hemicellulases (reviewed in Libby et al., 1994, supra). Preferred linkers are from glucoamylase from Aspergillus species and CBHI linkers from Tricoderma species. Preferably, the linker and the functional portion of the secreted polypeptide are from the same protein, although this is not required.

In an alternative embodiment, the secreted polypeptide does not include a terminal linker region. For example, when the full length secreted polypeptide is utilized as the second polypeptide, the desired polypeptide is fused to the C-terminus of the second polypeptide in the absence of an additional linker, although the secreted polypeptide may contain an internal linker. Similarly, a functional domain such as a catalytic domain may be used without a linker region as well.

Generally, when a functional portion of the secreted polypeptide is used as the second polypeptide, it is C-terminally truncated, i.e. contains an intact N-terminus. In alternate embodiments, the secreted polypeptide is N-terminally truncated, or optionally truncated at both ends to leave a functional portion.

In some cases, such as glucoamylase or proteases, the second polypeptide may be naturally produced as a proprotein which is subsequently processed by removal of the prosequence to yield the mature protein. In these cases, the prosequence naturally associated with the second polypeptide may or may not be included in the fusion polypeptide.

In some cases, such as glucoamylase or proteases, the second polypeptide may be naturally produced as a proprotein which is subsequently processed, by removal of the prosequence, to yield the mature protein. In these cases, the prosequence naturally associated with the second polypeptide may or may not be included in the fusion polypeptide.

Generally, such portions of the secreted polypeptide comprise greater than 50% of the secreted polypeptide, preferably greater than 75%, most preferably greater than 90% of the secreted polypeptide. Such portions comprise preferably the amino-terminal portion of the secreted polypeptide.

As indicated, the first nucleic acid encodes a signal polypeptide functional as a secretory signal in a first filamentous fungus. The signal sequences may be derived from a secreted polypeptide from a particular species of filamentous fungus. As also indicated, the second nucleic acid encodes a second amino acid sequence corresponding to all or part of a polypeptide normally secreted by either the first filamentous fungus (from which the signal polypeptide is obtained) or a second filamentous fungus (if the signal polypeptide and secreted polypeptide are from different filamentous fungi or if the signal polypeptide is obtained from a source other than a filamentous fungus, e.g. the chymosin signal from bovine species).

As used herein, "third nucleic acids" comprise nucleic acids encoding a cleavable linker polypeptide, which under certain circumstances, will allow the separation of the sequences bordering the cleavable linker. For example, sequences that are recognized and cleaved by a protease or cleaved after exposure to certain chemicals are considered cleavable linkers. For example, cleavable linkers include, but are not limited to, the prosequence of bovine chymosin, the prosequence of subtilisin, prosequences of retroviral proteases including human immunodeficiency virus protease and sequences recognized and cleaved by trypsin (EP 578472, Takasuga et al., J. Biochem. 112(5)652 (1992)) factor $X_a$ (Gardella et al., J. Biol. Chem. 265(26): 15854 (1990), WO 9006370), collagenase (J03280893, Tajima et al., J. Fermnent. Bioeng. 72(5): 362 (1991), WO 9006370), clostripain (EP 578472), subtilisin (including mutant H64A subtilisin, Forsberg et al., J. Protein Chem. 10(5): 517 (1991), chymosin, yeast KEX2 protease (Bourbonnais et al., J. Bio. Chem. 263(30): 15342 (1988), thrombin (Forsberg et al., supra; Abath et al., BioTechniques 10(2): 178 (1991)), *Staphylococcus aureus* V8 protease or similar endoproteinase-Glu-C to cleave after Glu residues (EP 578472, Ishizaki et al., Appl. Microbiol. Biotechnol. 36(4): 483 (1992)), cleavage by NIa proteinase of tobacco etch virus (Parks et al., Anal. Biochem. 216(2): 413 (1994)), endoproteinase-Lys-C (U.S. Pat. No. 4,414,332) and endoproteinase-Asp-N, Neisseria type 2 IgA protease (Pohlner et al., Bio/Technology 10(7): 799–804 (1992)), soluble yeast endoproteinase yscF (EP 467839), chymotrypsin (Altman et al., Protein Eng. 4(5): 593 (1991)), enteropeptidase (WO 9006370), lysostaphin, a polyglycine specific endoproteinase (EP 316748), and the like. See e.g. Marston, F.A.O. (1986) Biol. Chem. J. 240, 1–12. Particular amino acid sites that serve as chemical cleavage sites include, but are not limited to, methionine for cleavage by cyanogen bromide (Shen, PNAS USA 81: 4627 (1984); Kempe et al., Gene 39: 239 (1985); Kuliopulos et al., J. Am. Chem. Soc. 116: 4599 (1994); Moks et al., Bio/Technology 5: 379 (1987); Ray et al., Bio/Technology 11: 64 (1993)), acid cleavage of an Asp-Pro bond (Wingender et al., J. Biol. Chem. 264(8): 4367 (1989); Gram et al., Bio/Technology 12: 1017 (1994)), and hydroxylamine cleavage at an Asn-Gly bond (Moks supra).

Although cleavage at the fusion polypeptide to release the desired polypeptide will often be useful, it is not necessary. In those cases in which the desired polypeptide retains its functionality when it is part of the fusion polypeptide, cleavage may not be required or desirable. For this reason, the third amino acid sequence (and third nucleic acid) comprising the cleavable linker may be optional.

It should be understood that the third nucleic acid need only encode that amino acid sequence which is necessary to be recognized by a particular enzyme or chemical agent to bring about cleavage of the fusion polypeptide. Thus, the entire prosequence of, for example, chymosin or subtilisin need not be used. Rather, only that portion of the prosequence which is necessary for recognition and cleavage by the appropriate enzyme is required.

Particularly preferred cleavable linkers are the KEX2 protease recognition site (Lys-Arg), which can be cleaved by a native Aspergillus KEX2-like protease, trypsin protease recognition sites of Lys and Arg, and the cleavage recognition site for endoproteinase-Lys-C.

Us used herein, "fourth nucleic acids" encode "desired polypeptides." "Polypeptides" as used herein include proteins and peptides. Such desired polypeptides include, but are not limited to, enzymes, hormones, growth factors, cytokines, structural proteins and plasma proteins. Thus, preferred desired polypeptides include, but are hot limited to, bovine chymosin, human tissue plasminogen activator, human growth hormone, human interferon, human interleukin, human serum albumin, bacterial enzymes such as α-amylase from Bacillus species and lipase from Pseudomonas species, etc. Desired polypeptides further include fungal enzymes such as lignin peroxidase and $Mn^{2+}$-dependent peroxidase from Phanerochaete, glucoamylase from Humicola species and aspartyl proteases from Mucor species. Smaller polypeptides are also preferred, as is more generally outlined below, such as the anti-coagulant Hirudin and analogs such as R3-hirulog. Other suitable desired polypeptides include amylins and amylin antagonists, calcitonin, calcitonin gene-related peptides, glucagon, glucagon-like peptides, aprotinin, anti-bacterial peptides such as magainins, defensins and protegrins, somatostatin, atrial natriuretic peptide, brain natriuretic peptide, integrelin, epidermal growth factor, transforming growth factor α, insulin-like growth factor, various protein epitopes for use as vaccines.

In a preferred embodiment, the fourth nucleic acid comprises at least two coding nucleic acids each of which encode desired polypeptides. Generally, in this embodiment, the polypeptides range in size from about 2 to about 100 amino acids in length, with from about 10 to about 50 being preferred, and from about 15 to about 40 being particularly preferred. In alternative embodiments, the polypeptides are larger, i.e. are considered proteins. Additionally, from about two to about 20 desired polypeptides are used, with from about 2 to about 10 being preferred and from about 2 to about 5 being particularly preferred.

In this embodiment, the desired polypeptides may be the same polypeptide, i.e. identical polypeptides, or different polypeptides. That is, in one embodiment, the fourth nucleic acid comprises nucleic acids encoding multiple copies of a particular polypeptide. Alternatively, the fourth nucleic acid may encode single copies of several polypeptides, or multiple copies of several polypeptides.

When the fourth nucleic acid encodes at least two desired polypeptides, the coding regions for the polypeptides may be linked together directly, i.e. without intervening sequences such as those encoding cleavable linkers. For example, certain desired polypeptides may retain biological activity in a multimeric form. See for example U.S. Pat. No. 5,218,093, which describes the production of tandemly linked units of epidermal growth factor (EGF), which are produced as a single molecule.

In a preferred embodiment, the coding regions for the desired polypeptides of the fourth nucleic acid are separated by at least one intervening sequence, for example, an intervening sequence that encodes a cleavable linker. Preferably, each coding region for a desired polypeptide is separated from the next one by a nucleic acid encoding a cleavable linker. That is, when the fourth nucleic acid encodes two desired polypeptides, the coding region for the cleavable linker is positioned between the nucleic acids encoding the desired polypeptides. Similarly, a fourth nucleic acid encoding three desired polypeptides will have a cleavable linker sequence between each of the desired polypeptide sequences, i.e . two cleavable linker sequences; a fourth nucleic acid encoding four desired polypeptides will have three cleavable linker sequences, i.e. a cleavable linker sequence between each of the desired polypeptide sequences; a fourth nucleic acid encoding five desired polypeptides will have four cleavable linker sequences, i.e. a cleavable linker sequence between each of the desired polypeptide sequences, and so on.

In this embodiment, the cleavable linkers between the desired polypeptides may be the same or different from each other or the cleavable linker encoded by the third nucleic acid. That is, in one embodiment, the third nucleic acid encodes the same cleavable linker as is present between the desired polypeptides. Subjecting the fusion protein to the cleavage conditions releases all of the desired polypeptides. Alternatively, the cleavable linkers are different. That is, cleavage at the cleavable linker encoded by the third nucleic acid releases the fourth polypeptide from the secreted polypeptide but does not release the separate desired polypeptides encoded by the fourth nucleic acid. In some embodiments, the cleavable linkers between the desired polypeptides encoded by the fourth nucleic acids are different.

In an additional embodiment, the fourth nucleic acid further comprises a sequence encoding a polypeptide that facilitates purification of the fusion protein or desired polypeptides. The fourth nucleic acid may contain multiple copies of a nucleic acid encoding a purification polypeptide; for example, when the fourth nucleic acid comprises more than one desired polypeptide coding region, each nucleic acid encoding a desired polypeptide may additionally contain a coding region for a purification polypeptide. Thus, after cleavage or separation of the desired polypeptides, each desired polypeptide may utilize the exogeneous sequence for purification. Alternatively, there may be only one copy of the nucleic acid encoding a polypeptide used for purification per fusion nucleic acid. In this embodiment, for example, the purification polypeptide is used to purify the entire fusion polypeptide which then may be cleaved into a number of desired polypeptides if required. If necessary, the purification polypeptide may also be separated from the desired polypeptides by a cleavage polypeptide.

For example, sequences encoding specific epitopes may be included to allow purification via antibody columns, such as are known in the art. Similarly, sequences encoding proteins which bind to affinity chromatography columns may also be used. For example, Kuliopulos and Walsh (J. Am. Chem. Soc. 116: 4599 (1994)) produced a fusion protein which comprised a bacterial protein, a tandem repeat of a 13 amino acid peptide, and a carboxyl tag of six histidine residues. The $(His)_6$ tag allowed the fusion protein to be purified using Ni chelate chromatography. It is also possible to fuse peptides to proteins such as glutathione transferase (GST) or maltose binding protein and exploit the affinity purification methods available for these and other proteins in purification of the desired peptides.

In a preferred embodiment, the present invention provides fusion nucleic acids comprising, from 5' to 3', first, fifth, third and second nucleic acids. In this embodiment, the desired polypeptides are produced as N-terminal fusions rather than C-terminal, as described above. The first, third and second nucleic acids are as described above. A "fifth nucleic acid" encodes at least one desired polypeptide, as described above. Thus, in a preferred embodiment, a fifth nucleic acid encodes a single desired polypeptide. In alternate preferred embodiments, a fifth nucleic acid comprises at least two coding nucleic acids each of which encode desired polypeptides, as described above for fourth nucleic acids. When the fifth nucleic acid encodes more than one desired polypeptide, the fifth nucleic acid may also comprise intervening sequences such as third nucleic acids encoding cleavable linkers, as described above for fourth nucleic acids.

In a further preferred embodiment, the present invention provides fusion nucleic acids comprising from 5' to 3', a first nucleic acid and a second nucleic acid. The second nucleic acid comprises a first and a second part, separated by an insertion point. At the insertion point, an insertion nucleic acid is present. An "insertion nucleic acid" comprises a fifth nucleic acid and in some embodiments is flanked by third nucleic acids comprising cleavable linkers. That is, the fifth nucleic acid is inserted into the second nucleic acid with a third nucleic acid at the 5' end and another third nucleic acid at the 3' end of the fifth nucleic acid. In this embodiment, it is preferred that the fifth nucleic acid comprise a single nucleic acid encoding a desired polypeptide, although in alternate embodiments, additional nucleic acids encoding desired polypeptides and additional cleavable linkers may be included, as will be appreciated by those in the art and generally described above. In this embodiment, it is preferred that the second nucleic acid encode a secreted polypeptide that contains a linker region or domain, and that the insertion point be within this linker region. That is, as described above, some secreted polypeptides have functional domains separated by linker regions (not to be confused with cleavable linkers). Thus, preferred embodiments utilize secreted polypeptides that contain at least one functional domain and all or part of the linker region. Preferably, the entire secreted polypeptide including the linker region is used. The insertion point may be located anywhere within the linker region.

The above-defined nucleic acids encoding the corresponding amino acid sequences are combined to form a fusion nucleic acid. As so assembled, the nucleic acid will encode a "fusion polypeptide". In one embodiment, the fusion polypeptides comprise from its amino-terminus: a first amino acid sequence comprising a signal polypeptide functional as a secretory sequence in a filamentous fungus, a second amino acid sequence comprising a secreted polypeptide or functional portion thereof normally secreted from a filamentous fungus, a third amino acid sequence comprising a cleavable linker and a fourth amino acid sequence comprising at least two desired polypeptides. As will be appreciated by those in the art, the invention also includes polypeptides from which the signal sequence has been cleaved from the fusion polypeptide.

In an additional embodiment, the fusion polypeptides comprise from its amino-terminus: a first amino acid sequence comprising a signal polypeptide functional as a secretory sequence in a filamentous fungus, a fifth amino acid sequence comprising at least one desired polypeptides, a third amino acid sequence comprising a cleavable linker and a second amino acid sequence comprising a secreted polypeptide or functional portion thereof normally secreted from a filamentous fungus. As above, the invention also includes polypeptides from which the signal sequence has been cleaved from the fusion polypeptide.

In a further embodiment, the fusion polypeptide comprises from its amino terminus, a first amino acid sequence comprising a signal polypeptide functional as a secretory sequence in a filamentous fungus, and a second amino acid sequence. The second amino acid sequence comprises a first and a second part, separated by an insertion point. An insertion amino acid, comprising a fifth amino acid sequence flanked by third amino acid sequences, is inserted between the first and second parts of the second amino acid sequence, at the insertion point.

The fusion nucleic acids of the invention are constructed using well known techniques as is generally described in EPO Publication 0 215 594, incorporated by reference. Once made, the fusion nucleic acids are incorporated into any number of expression vectors as is known in the art. The expression vectors preferably contain regulatory sequences functional in the host to be transformed. Thus, in the case of filamentous fungus, such regulatory sequences include, but are not limited to, the transcriptional and translational regulatory sequences which may include, but are not limited to, promoter sequences, ribosomal binding sites, transcriptional start and stop sequences, polyadenylation signals, translational start and stop sequences, and enhancer or activator sequences. In a preferred embodiment, the regulatory sequences include a promoter and transcriptional start and stop sequences. As is appreciated in the art, the promoter and transcription and translation initiation sequences are operably linked to the 5' end of the fusion nucleic acid, and the transcription termination and polyadenylation sequences are operably linked to the 3' end of the fusion nucleic acid.

"Operably linked" in this context means that the transcriptional and translational regulatory DNA is positioned relative to the coding sequences in such a manner that transcription is initiated. Generally, this will mean that the promoter and transcriptional initiation or start sequences are positioned 5' to the coding region. The transcriptional and translational regulatory nucleic acid will generally be appropriate to the host cell used to express the fusion protein; for example, transcriptional and translational regulatory nucleic acid sequences from Aspergillus will be used to express the fusion protein in Aspergillus. Numerous types of appropriate expression vectors, and suitable regulatory sequences are known in the art for a variety of host cells.

Promoter sequences encode either constitutive or inducible promoters. The promoters may be either naturally occurring promoters or hybrid promoters. Hybrid promoters, which combine elements of more than one promoter, are also known in the art, and are useful in the present invention.

As used herein, a "promotor sequence" is a nucleic acid which is recognized by the particular filamentous fungus for expression purposes. It is operably linked to a nucleic acid encoding the above defined fusion polypeptide. Such linkage comprises positioning of the promoter with respect to the translation initiation codon of the nucleic acid encoding the fusion nucleic acid. The promoter sequence contains transcription and translation control sequences which mediate the expression of the fusion nucleic acid. Examples include the promoter from the *A. awamori* or *A. niger* glucoamylase genes (Nunberg, J. H. et al. (1984) Mol. Cell. Biol. 4, 2306–2315; Boel, E. et al. (1984) EMBO J. 3, 1581–1585), the *A. niger* and *A. oryzae* alpha-amylase genes (Korman et al. (1990) Curr. Genet 17, 203–212; Wirsel et al. (1989) Mol. Microbiol. 3, 3–14; Gines et al. (1989) Gene 79, 107–117; Tada et al. (1989). Biol. Agric Chem. 53, 593–599), the *Mucor miehei* carboxyl protease gene (EPO 0215594), the *Trichoderma reesei* cellobiohydrolase I gene (Shoemaker, S. P. et al. (1984) European Patent Application No. EPO0137280A1), the *A. nidulans* trpC gene (Yelton, M. et al. (1984) Proc. Natl. Acad. Sci. USA 81, 1470–1474; Mullaney, E. J. et al. (1985) Mol. Gen. Genet. 199, 37–45) the *A. nidulans* alcA gene (Lockington, R. A. et al. (1986) Gene 33, 137–149), the *A. nidulans* tpiA gene (McKnight, G. L. et al. (1986) Cell 46, 143–147), the *A. nidulans* amdS gene (Hynes, M. J. et al. (1983) Mol. Cell Biol. 3, 1430–1439), and higher eukaryotic promoters such as the SV40 early promoter (Barclay, S. L. and E. Meller (1983) Molecular and Cellular Biology 3, 2117–2130).

Likewise a "terminator sequence" is a nucleic acid which is recognized by the expression host to terminate transcription. It is operably linked to the 3' end of the fusion DNA encoding the fusion polypeptide to be expressed. Examples include the terminator from the *A. nidulans* trpC gene (Yelton, M. et al. (1984) Proc. Natl. Acad. Sci. USA 81, 1470–1474; Mullaney, E. J. et al. (1985) Mol. Gen. Genet. 199, 37–45), the *A. awamori* or *A. niger* glucoamylase genes (Nunberg, J. H. et al. (1984) Mol. Cell. Biol. 4, 2306–253; Boel, E. et al. (1984) EMBO J. 3, 1581–1585), the *A. niger* or *A. oryzae* alpha-amylase genes (Korman et al. supra; Wirsel et al. supra; Gines et al. supra; Tada et al. supra), and the *Mucor miehei* carboxyl protease gene (EPO Publication No. 0 215 594), although any fungal terminator is likely to be functional in the present invention.

A "polyadenylation sequence" is a nucleic acid which when transcribed is recognized by the expression host to add polyadenosine residues to transcribed mRNA. It is operably linked to the 3' end of the fusion DNA encoding the fusion polypeptide to be expressed. Examples include polyadenylation sequences from the *A. nidulans* trpC gene (Yelton, supra; Mullaney, supra), the *A. awamori* or *A. niger* glucoamylase genes (Nunberg, supra; Boel, supra), and the *Mucor miehei* carboxyl protease gene described above. Any fungal polyadenylation sequence, however, is likely to be functional in the present invention.

In addition, the expression vector may comprise additional elements. For example, the expression vector may have two replication systems, thus allowing it to be maintained in two organisms, for example in fungal cells for expression and in a procaryotic host for cloning and amplification. Furthermore, for integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The fusion proteins of the present invention are produced by culturing a host cell transformed with an expression vector containing fusion nucleic acid, under the appropriate conditions to induce or cause expression of the fusion protein. The conditions appropriate for fusion protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important.

Appropriate host cells include filamentous fungal cells. The "filamentous fungi" of the present invention, which serve both as the expression hosts and the source of the first and second nucleic acids, are eukaryotic microorganisms and include all filamentous forms of the subdivision Eumycotina, Alexopoulos, C. J. (1962), Introductory Mycology, New York: Wiley. These fungi are characterized by a vegetative mycelium with a cell wall composed of chitin, glucans, and other complex polysaccharides. The filamentous fungi of the present invention are morphologically, physiologically, and genetically distinct from yeasts. Vegetative growth by filamentous fungi is by hyphal elongation. In contrast, vegetative growth by yeasts such as *S. cerevisiae* is by budding of a unicellular thallus. *S. cerevisiae* has a prominent, very stable diploid phase whereas, diploids exist only briefly prior to meiosis in filamentous fungi like Aspergilli and Neurospora. *S. ceriviae* has 17 chromosomes as opposed to 8 and 7 for *A. nidulans* and *N. crassa* respectively. Recent illustrations of differences between *S. cerevisiae* and filamentous fungi include the inability of *S. cerevisiae* to process Aspergillus and Trichoderma introns and the inability to recognize many transcriptional regulators of filamentous fungi (Innis, M. A. et al. (1985) Science, 228, 21–26).

Various species of filamentous fungi may be used as expression hosts including the following genera: Aspergillus, Trichoderma, Neurospora, Penicillium, Cephalosporium, Achlya, Phanerochaete, Podospora, Endothia, Mucor, Fusarium, Humicola, Cochliobolus and Pyricularia. Specific expression hosts include *A. nidulans*, (Yelton, M., et al. (1984) Proc. Natl. Acad. Sci. USA, 81, 1470–1474; Mullaney, E. J. et al. (1985) Mol. Gen. Genet. 199, 37–45; John, M. A. and J. F. Peberdy (1984) Enzyme Microb. Technol. 6, 386–389; Tilburn, et al. (1982) Gene 26, 205–221; Ballance, D. J. et al., (1983) Biochem. Biophys. Res. Comm. 112, 284–289; Johnston, I. L. et al. (1985) EMBO J. 4, 1307–1311) *A. niger*, (Kelly, J. M. and M. Hynes (1985) EMBO 4, 475–479) *A. awamori*, e.g., NRRL 3112, ATCC 22342, ATCC 44733, ATCC 14331 and strain UVK 143f, *A. oryzae*, e.g., ATCC 11490, *N. crassa* (Case, M. E. et al. (1979) Proc. Natl. Acad. Scie. USA 76, 5259–5263; Lambowitz U.S. Pat. No. 4,486,553; Kinsey, J. A. and J. A. Rambosek (1984) *Molecular and Cellular Biology* 4, 117–122; Bull, J. H. and J. C. Wooton (1984) Nature 310, 701–704), *Trichoderma reesei*, e.g. NRRL 15709, ATCC 13631, 56764, 56765, 56466, 56767, and *Trichoderma viride*, e.g., ATCC 32098 and 32086. A preferred expression host is *A. awamori* in which the gene encoding the major secreted aspartyl protease has been deleted. The production of this preferred expression host is described in U.S. patent application Ser. No. 214,237 filed Jul. 1, 1988, expressly incorporated herein by reference.

The fusion nucleic acids are expressed as is known in the art to produce fusion proteins. In one embodiment, the fusion proteins comprise a signal polypeptide, a secreted polypeptide or functional portion thereof, one or more cleavable linkers and one or more desired polypeptides, combined as herein described. As will be appreciated by those in the art, the signal polypeptide may be cleaved off during expression to form a fusion protein, comprising a secreted polypeptide or functional portion thereof, a cleavable linker and at least two desired polypeptides, for example when the fusion polypeptide comprises (from N-terminus to C-terminus) a first, second, third and fourth polypeptide. The cleavable linker may then be cleaved using techniques known in the art, to release the desired polypeptide(s), with additional cleavage between multiple desired polypeptides done as required. The actual method of cleavage will depend on the cleavable linker selected.

In some embodiments, after cleavage via chemicals or endoproteinases, the desired polypeptides contain unwanted amino acids from the amino or carboxy termini. In this embodiment, a variety of aminopeptidases and carboxypeptidases of differing specificities may be used to remove the amino acids from the cleavable linker. Examples include, but are not limited to, pancreatic carboxypeptidase B to remove basic residues from the carboxyl terminus, soluble yeast carboxypeptidase-ysc-alpha (EP467839), carboxypeptidase E or N (WO 9206211 (in Japanese)), aminopeptidase A (WO 9206211 (in Japanese)), *Lactococcus lactis* dipeptidyl peptidase IV which removes prolyl-prolyl extensions from the amino terminus, X-prolyl dipeptidyl aminopeptidase from *Aspergillus oryzae* or *Lactococcus lactis* (Tachi et al., Phytochemistry 31(11): 3707 (1992); Yosphe-Besancon, Biotechnol. Appl. Biochem. 20(1): 131 (1994)).

The desired polypeptides may also be additionally purified or isolated if necessary, in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. Ultrafiltration and diafiltration techniques, in conjunction with protein concentration, are also useful. For general guidance in suitable purification techniques, see Scopes, R., Protein Purification, Springer-Verlag, NY (1982). Purification tags or sequences may also be used, as is known in the art. The degree of purification necessary will vary depending on the use of the desired polypeptide. In some instances no purification will be necessary.

The desired polypeptides may also be chemically modified, formulated for use or administration as needed, as will be appreciated by those in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The references cited herein are incorporated by reference.

EXAMPLES

General Methods
Methods for Aspergillus transformation

The expression plasmids designed for use with Aspergillus all contained the *A. niger* pyrG gene as selectable marker for transformation. This gene encodes orotidine 5'-monophosphate decarboxylase, an enzyme from the uridine biosynthetic pathway. The Aspergillus strains used were all pyrG mutant strains which consequently required uridin for growth. Selection for transformants involved growth in the absence of exogenous uridine. Purified plasmid DNA was digested with HindIII prior to transformation into Aspergillus.

Two different strains, GCGAP3-4 and dgr246 P2, were used in this work, both of which were derived from strain UVK143f (U.S. Pat. No. 5,364,770), a glucoamylase overproducing strain itself derived from strain NRRL3112. *A. niger* var *awamori* strain GCGAP3-4 has had the genes encoding the major secreted aspartic proteinase (pepA) and glucoamylase (glaA) deleted. Deletion of the glaA gene was achieved by transformation of strain GC12 (genotype pyrG5; argB3; described by Berka et al., 1991, in: Applications of Enzyme Biotechnology, Eds. Kelly, J. W. and Baldwin, T. O., Plenum Press, New York) with a linear DNA fragment having flanking regions of the glaA locus at either end with the glaA promoter and part of the coding region (from 245 bp 5' of the initiation codon to a position corresponding to codon 200 within the coding region) replaced by the pyrG gene from *Aspergillus nidulans*. One of the transformants in which this linear fragment had integrated at the glaA locus, inactivating the glaA gene, was called strain GCΔGAM64. The pepA gene was deleted from strain GCΔGAM64 by the same method as described by Berka et al. (1990, Gene 86: 153–162). This method involved transformation with a linear fragment of DNA comprising flanking regions of the pepA locus with the entire coding region (from 178 bp 5' of the initiation codon to approximately 900 bp 3' of the termination codon) replaced by the argB gene of *A. nidulans*. One of the transformants in which this DNA fragment had integrated at the pepA locus and inactivated the pepA gene was designated strain GCGAP3. A uridine requiring, pyrG deficient, derivative of strain GCGAP3 was selected by resistance to fluoroorotic acid (van Hartingsveldte et al. 1987, Mol. Gen. Genet. 206: 71–75) and called strain GCGAP3-4. It was observed by Southern analysis that a spontaneous deletion of DNA had occurred at the glucoamylase locus of this strain to remove the *A. nidulans* pyrG gene which had integrated at that site as well as some of the flanking regions of the glaA locus.

Strain dgr246 P2 has had the pepA gene deleted and is pyrG minus. In addition, strain dgr246 P2 has undergone several rounds of mutagenesis and screening or selection for improved production of a heterologous gene product. Both strains are described by Ward, M. et al. (1993) *A Microbiol Biotech*. 39: 738–743.

The transformation protocol is a modification of the Campbell method (Campbell et al. (1989). *Curr. Genet.* 16: 53–56) . All solutions and media were either autoclaved or filter sterilized through a 0.2 micron filter. Spores of *A. niger* var *awamori* were harvested from complex media agar (CMA) plates. CMA contained 20 g/l dextrose, 20 g/l DifcoBrand malt extract, 1 g/l Bacto Peptone, 20 g/l Bacto agar, 20 ml/l of 100 mg/ml arginine, 20 ml/l of 100 mg/ml uridine, 1 ml/l of 10 mg/ml PABA, 10 ml/l of met/bio solution, and 1 ml/l of 50 mg/ml streptomycin. Met/bio solution was composed of 50 g of L-methionine, 200 mg of D-biotin and distilled water up to 1 liter. An agar plug of approximately 1.5 cm square of spores were used to inoculate 100 mls of Yeast Extract Broth with glucose (YEG; 5 g/l yeast extract 20 g/l glucose, 20 ml/l 100 mg/ml arginine, 20 ml/l 100 mlg/ml uridine, 1 ml/l 50 mg/ml stretomycin). The flask was incubated at 37° C. on a shaker at 250–275 rpm, overnight. The mycelia were harvested through sterile Miracloth (Calbiochem, San Diego, Calif., USA) and washed with 200 mls of Solution A (0.8M $MgSO_4$ in 10 mM sodium phosphate, pH 5.8). The washed mycelia were placed in a sterile solution of 100 mg of Novozym234 (Novo Nordisk Industri A/S, Copenhagen, Denmark) in 20 mls of solution A. This was incubated at 28° C. at 200 rpm for 1 hour in a sterile 250 ml plastic bottle (Corning Inc, Coming, N.Y.). After incubation, the protoplasting solution was filtered through sterile Miracloth into a sterile 50 ml conical tube (Sarstedt, USA). The resulting liquid containing protoplasts was divided equally amongst 4–50 ml conical tubes. Forty mls of solution B (1.2 M sorbitol, 50 mM $CaCl_2$, 10 mM Tris, pH7.5) were added to each tube and centrifuged in a table top clinical centrifuge (Damon IEC HN SII centrifuge) at ¾ speed for 10 minutes. The supernatant from each tube was discarded and 20 mls of fresh solution B was added to one tube, mixed, then poured into the next tube until all the pellets were resuspended. The tube was then centrifuged at ¾ speed for 10 minutes. The supernatant was discarded, 20 mls of fresh solution B was added, the tube was centrifuged for 10 minutes at ¾ speed. The wash occurred one last time before resuspending the washed protoplasts in solution B at a density of 0.5–1.0×107 protoplasts/100 ul. To each 100 ul of protoplasts in a sterile 15 ml conical (Sarstedt, USA), 10 ul of the transforming plasmid DNA was added. To this, 12.5 ul of solution C (50% PEG 4000, 50 mM $CaCl_2$, 10 mM Tris, pH 7.5) was added and the tube was placed on ice for 20 minutes. One ml of solution C was added and the tube was removed from the ice to room temperature and shaken gently. Two mls of solution B was added immediately to dilute solution C. The transforming mix was added equally to 3 tubes of melted MMS overlay (6 g/l $NaNO_3$, 0.52 g/l KCl, 1.52 g/l $KH_2PO_4$, 218.5 g/l D-sorbitol, 1.0 ml/l trace elements-LW, 10 g/l SeaPlaque agarose (FMC Bioproducts, Rockland, Me., USA) 20 ml/l 50% glucose, 2.5 ml/l 20% $MgSO_4*7H_2O$, 10 ml/l met/bio solution, 2.0 ml/l 10 mg/ml PABA pH to 6.5 with NaOH) that were stored in a 37° C. water bath. Trace elements LW consisted of 1 g/l $FeSO_4.7H_2O$, 8.8 g/l $ZnSO_4.7H_2O$, 0.4 g/l $CuSO_4.5H_2O$, 0.15 g/l $MnSO_4.4H_2O$, 0.1 g $Na_2B_4O_7$. $10H_2O$, 50 mg/l $(NH_4)_6Mo_7O_{24}.4H_2O$, 250 mls $H_2O$, 200 ul/l concentrated HCl. The melted overlays with the transformation mix were immediately plated onto 3 MMS plates (same as MMS overlay recipe with the exception of 20 g/l of Bacto agar instead of 10 g/l of SeaPlaque) that had been supplemented with 200 ul/plate of 100 mg/ml of arginine added directly on top of the agar plate. After the agar solidified, the plates were incubated at 37° C. until transformants grew.

The sporulating transformants were picked off with a sterile toothpick onto a plate of minimal media+glucose (MM). MM consisted of 6 g/l NaNO$_3$, 0.52 g/l KCl, 1.52 g/l KH$_2$PO$_4$, 1 ml/l Trace elements LW, 20 g/l Bacto agar, pH to 6.5 with NaOH, 25 ml/l of 40% glucose, 2.5 ml/l of 20% MgSO$_4$.7H$_2$O, 1 ml/l of 50 mg/ml stretomycin/10 mg/ml carbenicillin, 20 ml/l of 100 mg/ml arginine. Once the transformants grew on MM they were transferred to CMA plates.

Each transformant was given a designation which included the host strain, either GAP3-4 (=GCGAP3-4) or dgr246 (=dgr246 P2), the plasmid used for transformation, e.g. GAKHiH (=pGAKHiH+) and a number to distinguish individual transformants. As an example, transformant #3 obtained from strain GCGAP3-4 with plasmid pGAKHi+ would be designated GAP3-4GAKHiH+ #9.

Methods for culture of Aspergillus transformants in shake flasks

A 1.5 cm square agar plug of each strain was added to 50 mls, in a 250 ml shake flask, of an inoculum medium called CSL+fructose (100 g/l corn steep liquor (50% solids, National), 1 g/l NaH$_2$PO$_4$.H$_2$O, 0.5 g/l MgSO$_4$, 100 g/l maltose, 10 g/l glucose, 50 g/l fructose, 3 ml/l Mazu DF60-P (Mazur Chemicals, Gurnee, Ill., USA), pH to 5.8 with NaOH, 1 ml/l of 50 mg/ml streptomycin/10 mg/ml carbenicillin. Flasks were incubated at 37° C., 200 rpm, for 2 days. Five mls of the 2 day old medium were inoculated into 50 ml of one of two different possible production media; called either Clofine special or Sheftone N. Clofine special had the following components: 70 g/l sodium sitrate, 15 g/l (NH$_4$)$_2$ SO$_4$, 1 g/l NaH$_2$PO$_4$.H$_2$O, 1 g/l MgSO$_4$, 1 ml Tween 80, pH to 6.2 with NaOH, 2 ml/l Mazu DF60-P, 60 g/l spray dried tofu TF30 soy milk powder (Armour Good Ingredients, Springfield, Ky., USA), 120 g/l maltose, 20 ml/l of 100 mg/ml arginine. Sheftone N medium had the following components: 100 g/l Sheftone N (Sheffield Products, Norwich, N.Y., USA); 13.6 g/l (NH$_4$)$_2$SO$_4$; 0.8 g/l MgSO$_4$; 1 g/l KCl; 1 g/l KH$_2$PO$_4$; 120 g/l sodium citrate; 1 ml Tween 80; 13 ml/i Mazu DF60-P; 10 g/l glucose; 100 g/l maltose, 20 ml/l of 100 mg/ml arginine. The production media flasks were incubated at 37° C., 200 rpm for up to 5 days and supernatant samples were taken for analysis at various times throughout.

Detection of glucoamylase-polypeptide fusion proteins produced by Aspergillus transformants Five $\mu$l samples of culture supernatant were mixed with 15 $\mu$l of running buffer, and 5 $\mu$l of tracking dye and subjected to sodium dodecyl sulfate (SDS)-polyacrylamide gel electrophoresis using precast gels according to the manufacturers instructions (Daiichi or Novex). The gels were either stained for protein with Coomassie stain or the protein was transferred to nitrocellulose filters by Western blotting (Towbin et al., 1979, Proc. Natl. Acad. Sci. USA 76: 4350–4354). Glucoamylase was visualized on Western blots by sequential treatment with rabbit anti-glucoamylase antibody and goat anti-rabbit IgG conjugated with horse radish peroxidase (HRP) followed by HRP color development by incubation with H$_2$O$_2$ and 4-chloro-1-napthol. The presence of hemagluttinin (HA) epitope on glucoamylase-HA epitope fusion proteins transferred to Western blots was detected by sequential treatment with a monoclonal mouse anti-HA antibody (clone 12CA5, Boehringer Mannheim, Indianapolis, Ind., USA) and goat anti-mouse IgG conjugated with horse radish peroxidase (HRP) followed by HRP color development by incubation with H$_2$O$_2$ and 4-chloro-1-napthol.

As an initial screen, transformants were cultured in Clofine special production medium for 4 or 5 days. Under these conditions, the glucoamylase-polypeptide fusion proteins appeared on Coomassie stained gels or on Western blots as lower in molecular weight than full-length glucoamylase and, thus, could be distinguished from native glucoamylase. This was the case even if the predicted molecular weight of the glucoamylase-polypeptide fusion protein was similar to glucoamylase (e.g., the expected product from pGA(KHi)$_5$+ transformants described in Example 3. The lower than predicted molecular weight of some of the glucoamylase-hirulog fusion proteins was presumed to be due to proteolysis. Proteolysis of glucoamylase-polypeptide fusion proteins in liquid culture was minimized by using Sheftone N production medium, by production in strain dgr246 P2 as compared to strain GCGAP3-4, and by examining glucoamylase-polypeptide products at early time points during culture (there was less effect of proteolysis at earlier time points, i.e., before 5 days of culture, although yields were lower).

Using the Western blot method it was possible to identify those transformants of GAP3-4 which produced glucoamylase-polypeptide fusion proteins since the untransformed parent strain produced no native glucoamylase. The polyclonal anti-glucoamylase antibody had much greater affinity for full-length glucoamylase bearing the starch binding domain than it did for forms of glucoamylase without the starch binding domain. As a result, it was also possible to identify those transformants of strain dgr246 P2 in which the expression vector had integrated at the glaA locus since these transformants made no full-length glucoamylase and only showed the weaker staining on Western analysis associated with glucoamylase-hirulog fusion proteins. However, in the majority of transformants the expression vector integrated at unknown sites in the genome rather than at the glaA locus. All the transformants described in greater detail below were of this type.

It was possible to identify the Coomassie-stained protein band corresponding to the glucoamylase-polypeptide fusion protein i transformants of GCGAP3-4 or dgr 246 P2 obtained with any of the expression vectors by comparison with supernatant from the untransformed control strains. Those transformants which produced the greatest amount of glucoamylase-hirulog as judged by the protein gels or Western blots were identified and used for further studies.

Polypeptides were purified by reverse phase HPLC and sequence analysis and mass spectrometer analysis performed as follows. Samples were applied to a Vydec 218TP54 reverse phase HPLC column, using a Hewlett Packard 1090M HPLC system. The mobile phase was 0.1% TFA (trifluoroacetic acid) and the organic phase was 0.08% TFA in acetonitrile. The gradient was run to 60% acetonitrile at 0.5% /min after a 5 minute initial wash. Peaks of interest were collected by hand at the appropriate times and submitted for sequence analysis and mass spectrometer analysis.

Tryptic digestion of polypeptides was performed as follows. To 200 micrograms of protein, 1N HCl was added to a final concentration of 0.1N and the sample was incubated on ice for 10 minutes. The denatured protein was precipitated by the addition of 9 volumes of 100% acetone and centrifugation at 13,000×g. The supernatant was removed and the pellet washed with 500 microliters of 80% acetone. Forty microliters of 8M urea in 1M Tris (pH 8.53 with TFA) was added to dissolve the pellet, followed by 160 microliters of deionized water and 8 microliters of 1 mg/ml trypsin (Worthington Labs) in 0.1M Hcl. The sample was incubated at 37° C. for 2 hours. Upon completion, the reaction was terminated by the addition of 10% TFA to a final concentration of 1%.

Sequence analysis of peptides was performed on an ABI automated sequencer using the Edman degradation chemistry.

For mass spectrometry analysis 50 microliters of polypeptide collected from HPLC was mixed with acetic acid to give a final acetic acid concentration of 1%. This sample was introduced to a Hewlett Packard model 55987 Electrospray Mass Spectrrometer through a 50 microliter loop attached to a Valco manual injection valve. The pump providing flow was a Hewlett Packard 1090M HPLC running at 0.05 ml/min. Mass data was collected and analyzed using Hewlett Packard ChemStation Data Analysis Software.

EXAMPLE 1

Assembly of Single and Tandem Repeats of R3-Hirulog Coding Sequences

We have tested the production of fusion proteins consisting of Aspergillus glucoamylase, or portions thereof, coupled to single copies or tandem repeats of the peptide R3-hirulog. This peptide consists of 18 amino acids with the following sequence: RPGGGGNGDFEEIPEEYL (SEQ ID NO: 17). Between glucoamylase and the peptide and between individual peptide units in a tandem array either a lysine (K) or lysine+arginine (KR) were positioned. In some cases we positioned a lysine followed by five histidine residues at the carboxyl end of the fusion protein. Oligonucleotides were synthesized and assembled in order to encode the following combinations of elements where K=lysine, R=arginine, H=histidine, X=R3-hirulog.

K—X (SEQ ID NO: 6)

K—X—K(H)$_5$ (SEQ ID NO: 7)

K—X—K—X—K—X—K—X—K—X (SEQ ID NO: 18)

KR—X—KR—X—KR—X—KR—X—KR—X (SEQ ID NO: 19)

The rationale for proteolytic cleavage of these polypeptides to release monomeric forms of R3-hirulog is as follows. Trypsin will cleave on the carboxyl side of basic residues (i.e., either Arg or Lys) and KEX2 proteinase will cleave on the carboxyl side of dibasic residues (i.e., Lys-Arg). However, it is expected that, in common with other serine proteinases, neither trypsin nor KEX2 proteinase will cleave the polypeptide if the amino acid on the carboxyl side of the cleavage site is a proline. Endoproteinase-Lys-C would be expected to cleave on the carboxyl side of lysine residues. The polypeptides above which have the Lys-Arg sequence of amino acids before or between R3-hirulog monomers would be expected to be cleaved by Aspergillus KEX2 proteinase within the secretory apparatus of Aspergillus. Those polypeptides with only a Lys residue separating glucoamylase and the R3-hirulog monomers would not be expected to be cleaved by KEX2 proteinase but could be cleaved in vitro with either trypsin or endoproteinase-Lys-C after the Lys residues. In all cases mentioned above, the product of cleavage would be R3-hirulog with either one basic residue (Lys) or two basic residues (Lys-Arg) at the carboxyl terminus. These basic residues could be removed from R3-hirulog by the action of, for example, carboxypeptidase B, which will remove basic residues from the carboxyl terminus of peptides.

The double-stranded synthetic DNA molecules encoding the above sequences were designed either to have a single-strand overhang compatible for ligation with NheI restricted DNA at the 5' end and a single-strand overhang compatible with BstEII restricted DNA at the 3' end or single-strand overhangs compatible with NheI restricted DNA at both ends.

Several pairs of complementary oligonucleotides were synthesized with the following sequences.

Oligonucleotide pair 1 encodes an NheI compatible overhang, a lysine, the first 13 amino acids of R3-hirulog, and has an XmaI compatible overhang at the 3' end.

HirK1-A: 5'-CTAGCAAGCGCCCCGGCGGCGGCG
GCAACGGCGACTTCGAGGAGATC (SEQ ID NO: 20)

HirK1-B:
5'-CCGGGATCTCCTCGAAGTCGCCGTTGC
CGCCGCCGCCGGGGCGCTTG (SEQ ID NO: 21)

Oligonucleotide pair 2 encodes an NheI compatible overhang, lysine and arginine, the first 13 amino acids of R3-hirulog, and has an XmaI compatible overhang at the 3' end.

HirKR1-A:
5'-CTAGCAAGCGCCGCCCCGGCGGCGGCG
GCAACGGCGACTTCGAGGAGATC (SEQ ID NO: 22)

HirKR1-B:
5'-CCGGGATCTCCTCGAAGTCGCCGTTGCC
GCCGCCGCCGGGGCGGCGCTTG (SEQ ID NO: 23)

Oligonucleotide pair 3 encodes the last 5 amino acids of R3-hirulog, a lysine residue, and the first 13 amino acids of R3-hirulog. It has BspEI or XmaI compatible overhangs at both ends.

Hir2-A:
5'-CCGGAGGAGTACCTGAAGCGCCCCGGCGG
CGGCGGCAACGGCGACTTCGAGGAGATC

Hir2-B: (SEQ ID NO: 24)
5'-CCGGGATCTCCTCGAAGTCGCCGTTGCCGC
CGCCGCCGGGGCGCTTCAGGTACTCCT (SEQ ID NO: 25)

Oligonucleotide pair 4 encodes the last 5 amino acids of R3-hirulog, a stop codon, a BstEII recognition site and has an XmaI compatible overhang at the 5' end and an EcoRI compatible overhang at the 3' end.

Hir3-A: 5'-CCGGAGGAGTACCTGTAGGTGACCG (SEQ ID NO: 26)

Hir3-B: 5'-AATTCGGTCACCTACAGGTACTCCT (SEQ ID NO: 27)

Oligonucleotide pair 5 encodes the last 5 amino acids of R3-hirulog, a lysine residue, five histidine residues, a stop codon, a BstEII recognition site and has an XmaI compatible overhang at the 5' end and an EcoRI compatible overhang at the 3' end.

Hir3-5H-A:
5'-CCGGAGGAGTACCTGAAGCACCACCAC
CACCACTAGGTGACCG (SEQ ID NO: 28)

Hir3-5H-B:
5'-AATTCGGTCACCTAGTGGTGGTGGTGGT
GCTTCAGGTACTCCT (SEQ ID NO: 29)

Each oligonucleotide pair was annealed and the DNA ends phosphorylated using polynucleotide kinase. The resulting double-stranded DNA molecules were ligated with pSL1180 which had been digested with appropriate restriction endonucleases (see below) and dephosphorylated using alkaline phosphatase.

Oligonucleotide pair 1 was ligated with pSL1180 which had been cut with NheI and XmaI to give plasmid pSL-HirK1.

Oligonucleotide pair 2 was ligated with pSL1180 which had been cut with NheI and XmaI to give plasmid pSL-HirKR1

Oligonucleotide pair 3 was ligated with pSL1180 which had been cut with BspEI and XmaI to give plasmid pSL-HirK2.

Oligonucleotide pair 4 was ligated with pSL11809 which had been cut with BspEI and EcoRI to give plasmid pSL-Hir3.

Oligonucleotide pair 5 was ligated with pSL11809 which had been cut with BspEI and EcoRI to give plasmid pSLHir3-5H.

FIG. 2 (SEQ ID NOS: 1–5) shows diagrams of the above five plasmids containing synthetic DNA and shows the important restriction sites and the amino acids encoded by the oligonucleotides. In each case DNA sequence analysis confirmed that the sequence of the oligonucleotides was as expected and that, in the case of pSLHirK2, that the oligonucleotides were inserted in the desired orientation in the multiple cloning site of pSL1180.

In order to create a plasmid containing DNA encoding a complete R3-hirulog peptide preceeded by a lysine residue pSLHirK1 was digested with XmaI and EcoRI, the large DNA fragment was isolated and was dephosphorylated using alkaline phosphatase. This DNA was ligated with oligonucleotide pair 4 which had been purified by agarose gel electrophoresis after digestion of pSLHir3 with BspEI and EcoRI. The resulting plasmid was named pA3 (FIG. 3) (SEQ ID NOS: 6–7).

In order to create a plasmid containing DNA encoding a complete R3-hirulog peptide preceeded by a lysine residue and with a lysine and five histidine residues at the carboxyl terminus pSLHirK1 was digested with XmaI and EcoRI, the large DNA fragment was isolated and was dephosphorylated using alkaline phosphatase. This DNA was ligated with oligonucleotide pair 5 which had been purified by agarose gel electrophoresis after digestion of pSLHir3-5H with BspEI and EcoRI. The resulting plasmid was named pA2 (FIG. 3) (SEQ ID NOS: 6–7).

Creation of tandem repeats of the R3-hirulog encoding sequence was performed as follows. Plasmid pSLHirK2 was digested with BspEI and DraIII, the DNA ends were dephosphorylated with alkaline phosphatase and the larger DNA fragment was isolated from an agarose gel. The same plasmid, pSLHirK2, was also cut with XmaI and DraIII and the smaller of the two DNA fragments was purified from an agarose gel. These two DNA fragments were ligated to create the plasmid pSLHirK2X2 (FIG. 4). This plasmid contained two tandem copies of oligonucleotide pair 3 and thus encoded the last 5 residues of R3-hirulog, a lysine residue, a complete R3-hirulog peptide, a lysine residue, and the first 13 residues of R3-hirulog.

Plasmid pSLHirK2X2 was digested with BspEI and DraIII, the DNA ends were dephosphorylated with alkaline phosphatase and the larger DNA fragment was isolated from an agarose gel. The same plasmid, pSLHirK2X2, was also cut with XmaI and DraIII and the smaller of the two DNA fragments was purified from an agarose gel. These two DNA fragments were ligated to create the plasmid pSLHirK2X4 (FIG. 4) (SEQ ID NOS: 8–9). This plasmid contained four tandem copies of oligonucleotide pair 3 and thus encoded the last 5 residues of R3-hirulog, a lysine residue, three complete R3-hirulog peptides separated by lysine residues, a lysine residue, and the first 13 residues of R3-hirulog.

In order to create a plasmid containing DNA encoding five copies of R3-hirulog preceeded and separated by lysine residues the following strategy was employed. Plasmid pSLHirK1 was digested with XmaI and EcoRI, the DNA ends were dephophorylated and the large DNA fragment was purified after agarose gel electrophoresis. Plasmid pHirK2X4 was digested with BspEI and EcoRI and the smaller DNA fragment was purified. These two fragments were ligated to form pK1,K2X4 (FIG. 5) (SEQ ID NOS: 10–11). This plasmid, pK1,K2X4 was then digested with XmaI and EcoRI, the DNA was dephosphorylated, and the large fragment was purified. Plasmid pSLHir3 was digested with BspEI and EcoRI and the small DNA fragment was purified. Ligation of these two fragments created pK1,K2X4,3 (FIG. 5) (SEQ ID NOS: 10–11).

In order to create a plasmid containing DNA encoding five copies of R3-hirulog separated by lysine, preeceeded by lysine and arginine, and with a lysine and five histidine residues at the carboxyl end the following strategy was employed. Plasmid pSLHirKR1 was digested with XmaI and EcoRI, the DNA ends were dephophorylated and the large DNA fragment was purified after agarose gel electrophoresis. Plasmid pHirK2X4 was digested with BspEI and EcoRI and the smaller DNA fragment was purified. These two fragments were ligated to form pKR1,K2X4 (FIG. 6) (SEQ ID NOS: 12–13). This plasmid, pKR1,K2X4 was then digested with XmaI and EcoRI, the DNA was dephosphorylated, and the large fragment was purified. Plasmid pSLHir3-5H was digested with BspEI and EcoRI and the small DNA fragment was purified. Ligation of these two fragments created pKR1,K2X4,3H (FIG. 6) (SEQ ID NOS: 12–13).

In the above examples R3-hirulog encoding peptides were assembled in a manner designed to allow their in-frame fusion at the 3' end of the glucoamylase coding region and thus included a translation stop codon near the 3' end of the synthetic DNA. It was also necessary to designed R3-hirulog encoding oligonucleotides which could be inserted at an internal position within the glucoamylase coding region without disrupting the reading frame. For this purpose it was desired that the oligonucleotides would encode R3-hirulog preceeded, separated by and followed by lysine residues as shown below where K=lysine, X=R3-hirulog.

K—X—K (SEQ ID NO: 14)

The following pair of oligonucleotieds was synthesized.

Oligonucleotide pair 6 encodes the last 5 amino acids of R3-hirulog followed by a lysine residue, has an XmaI compatible overhang at the 5' end and an NheI compatible overhang at the 3' end.

Hir3K-A: 5'-CCGGAGGAGTACCTGAAGGCTAGCG (SEQ ID NO: 30)

Hir3K-B: 5'-AATTCGCTAGCCTTCAGGTACTCCT (SEQ ID NO: 31)

In order to create a plasmid containing DNA encoding a complete R3-hirulog peptide preceeded and followed by a lysine residue plasmid pSLHirK1 was digested with XmaI and EcoRI, the DNA ends were dephosphorylated using alkaline phosphatase and the large DNA fragment was purified from an agarose gel. This DNA fragment was ligated with annealed oligonucleotide pair 6, the 5' ends of which had been phosphorylated using polynucleotide kinase, to create plasmid pK1,3K (FIG. 7) (SEQ ID NO: 14).

EXAMPLE 2

Design of Oligonucleotides Encoding HA Epitope

Oligonucleotides were designed to encode a nine amino acid epitope of hemagluttinin (HA) with the following sequence: YPYDVPDYA (SEQ ID NO: 32). The design of the oligonucleotides ultimately allowed this amino acid sequence to be fused at the amino terminus of glucoamylase (followed by a methionine residue) or to be inserted into the linker region of glucoamylase (preceeded by a lysine residue and followed by a methionine residue).

Two pairs of complementary oligonucleotides were synthesized with the following sequences.

Oligonucleotide pair 7 encodes an NheI compatible overhang, a lysine residue, the 9 amino acids of HA epitope, a methionine residue, and has an NheI compatible overhang at the 3' end.

K-EPI-M-A:
5'-CTAGCAAGTACCCCTACGATGTGCCCGA CTACGCTATGG (SEQ ID NO: 33)

K-EPI-M-B:
5'-CTAGCCATAGCGTAGTCGGGCACATCGTA GGGGTACTTG (SEQ ID NO: 34)

Oligonucleotide pair 8 encodes a BssHII compatible overhang, alanine, lysine and arginine residues, the 9 amino acids of HA epitope, a methionine residue, and has a BssHII compatible overhang at the 3' end.

NEPI-A:
5'-CGCGCTAAGCGCTACCCCTACGATGTGCC CGACTACGCTATG. (SEQ ID NO: 35)

NEPI-B:
5'-CGCGCATAGCGTAGTCGGGCACATCGTA GGGGTAGCGCTTAG. (SEQ ID NO: 36)

Oligonucleotide pair 7 was ligated with pSL1180 which had been cut with NheI to give plasmid pEpiN (FIG. 8) (SEQ ID NOS: 15–16).

Oligonucleotide pair 8 was ligated with pLitmus29 (New England Biolabs, Beverly, Mass., USA) which had been cut with BssHII to give plasmid pLit29+Nepi (FIG. 8) (SEQ ID NOS: 15–16).

EXAMPLE 3

Construction of the pGA+Plasmid Series, a Series of Expression Vectors Containing Polypeptide-encoding Sequences Fused to the Linker Region of Glucoamylase A series of expression plasmids was constructed, using methods known in the art, designed to produce fusion proteins consisting of desired polypeptides fused to the C-terminus of the catalytic core and part of the linker region of Aspergillus glucoamylase.

The pGA+ series of plasmids were constructed based on the bacterial plasmid pSL1180 (Pharmacia LKB). This plasmid is similar to the pUC series of phagemids such as pUC118 but has an extended multiple cloning site (MCS) containing all possible six base pair palindromes including two recognition sites for ClaI, one of which is methylated and the other not methylated by E. coli dam methylase. An expression cassette was inserted into the MCS of pSL1180 so that the first 28 bp of the MCS from HindIII to SpeI was present at one end. Beginning at the SpeI recognition site the expression cassette contains the following components: the promoter and 5' flanking region of the glaA gene of A. niger var. awamori strain UVK143f (U.S. Pat. No. 5,364,770) starting at a SpeI site approximately 1 kb upstream from the translation start codon; the coding region of the glaA gene from strain UVK 143f from the start codon to an NheI site, the six bp of which encode amino acids 497 and 498 in the linker region of mature glucoamylase; a synthetic piece of double stranded DNA encoding the desired peptide with NheI and BstEII ends; approximately 250 bp of the terminator region of the glaA gene from A. niger strain #7 (U.S. Pat. No. 5,364,770) beginning at a BstEII site 20 bp 5' of the translation stop codon and ending at an EcoRV site; an approximately 2.4 kb fragment containing the A. niger pyrG gene (Wilson et al., 1988) obtained as a SmaI to ScaI fragment from pBH2 (Ward et al., 1989) ( the SmaI site exists within the pUC18 MCS of pBH2 and the ScaI site exists 65 bp from the end of the BamHI-HindIII fragment of A. niger DNA present in pBH2); approximately 1.3 kb of 3' flanking DNA from the glaA gene of A. niger, beginning at the EcoRV site 250 bp 3' of the translation stop codon and ending at a ClaI site. After the ClaI site there exists 75 bp of the pSL1180 MCS from ClaI (the site not methylated by E. coli dam methylase) to HindIII, followed by 6 bp of pBR322 from HindIII to ClaI, followed by 198 bp of the pSL1180 MCS from ClaI (the site methylated by E. coli dam methylase) to EcoRI.

As shown in FIG. 9 these expression vectors (pGA+ series) contain unique NheI and BstEII sites which can be utilized to insert a DNA fragment encoding any desired peptide such that a fusion protein (comprising the glucoamylase catalytic core, part of the glucoamylase linker region and the desired peptide) would be expected to be produced after transformation into Aspergillus strains. The pyrG gene is included as a selectable marker for transformation into Aspergillus strains which are pyrG null mutants.

The NheI-BstEII pieces of synthetic DNA encoding R3-hirulog peptide or tandem repeats thereof were isolated from plasmids pA2; pA3; pK1,K2X4,3; and pKR1,K2X4, 3H and were inserted into the pGA+ series plasmid at the unique NheI and BstEII sites to form pGAKHiH+, pGAKHi+, pGA(KHi)$_5$+, and pGAKR(KHi$_5$)H+ respectively (FIG. 9).

For control experiments an expression plasmid designed to produce in Aspergillus a truncated version of glucoamylase (residues 1–498 of mature glucoamylase with a lysine residue at the C-terminus but with no attached polypeptide) was constructed by the following steps. A pair of oligonucleotides with the following sequences were synthesized.

GAD3'-A: 5'-CTAGCAAGTAG (SEQ ID NO: 37).
GAD3'-B: 5'-GTCACCTACTTG (SEQ ID NO: 38).

The above oligonucleotide pair was annealed, the DNA ends were phosphorylated with polynucleotide kinase and it was inserted into the pGA+ series plasmid at the unique NheI and BstEII sites to form pGAΔ3'.

Plasmids pGAKHiH+, pGAKHi+, pGA(KHi)$_5$+, pGAKR (KHi$_5$)H+ and pGAΔ3' were transformed into strains GCGAP3-4 or dgr246 P2 and the transformants were sereened for glucoamylase production as described in the General Methods section. The following transformants were selected for further study.

GAP3-4GAKHiH+ #9
GAP3-4GA(KHi)$_5$+ #10
GAP3-4GAKR(KHi)$_5$H+ #7
dgr246GAKHiH+ #3
dgr246GA(KHi)$_5$+ #11
dgr246GAKR(KHi$_5$)H+ #14
GAP3-4GAΔ3' #2

With appropriate transformants, it was possible to confirm that a single copy or five tandem repeats of R3-hirulog remained attached to glucoamylase in supernatant samples by demonstration of the presence of a histidine tail at the carboxyl terminus or by determination of the size of the glucoamylase-hirulog fusion protein produced. The results are summarized below. Two forms of glucoamylase, GAI and GAII, are naturally present in the supernatant of Aspergillus niger cultures. On SDS-PAGE these forms have apparent molecular weights of approximately 69 kDa and 48 kDa. The molecular weight of the truncated form of glucoamylase produced by transformant GAP3-4GAΔ3' #2 had an apparent molecular weight of 47 kDa, as estimated by gel electrophoresis.

Transformants GAP3-4GAKHiH+ #9 and dgr246GAKHiH+ #3 were cultured in Sheftone N medium for 2 to 3 days. A single additional protein band, compared to untransformed control strains, was observed following electrophoretic separation of the secreted proteins. This protein was of a similar size (approximately 48 kDa) as the glucoamylase protein produced by transformant GAP3-4GAΔ3' #2. It was possible to purify some of the 48 kDa protein produced by transformants GAP3-4GAKHiH+ #9 and dgr246GAKHiH+ #3 using the following approach. Supernatant samples were desalted using PD-10 Columns (Pharmacia Biotech, Piscataway, N.J., USA). A buffer comprising 50 mM sodium phosphate, pH8.0, 300 mM NaCl, 20 mM imidazole, 1 mMPMSF was used to equilibrate these columns and to elute the protein samples. Qiagen Ni-NTA spin columns (Qiagen, Chatsworth, Calif., USA) were then used according to the manufacturers instructions to purify any proteins with a polyhistidine tail. Protein samples purified in this manner were concentrated using Microcon 3 concentrators (Amicon). A single 48 kDa protein was purified from culture supernatants of both of these transformants. However, it was not possible to purify a protein of any size from GAP3-4GAΔ3' #2 using the Ni-NTA spin columns. These experiments demonstrated that the desired glucoamylase-hirulog fusion protein (i.e., glucoamylase catalytic core and linker region with one copy of R3-hirulog and five histidine residues at the carboxyl terminus) is produced by transformants GAP3-4GAKHiH+ #9 and dgr246GAKHiH+ #3.

Transformants GAP3-4GAKR(KHi$_5$)H+ #7 and dgr246GAKR(KHi$_5$)H+ #14 were cultured in Sheftone N medium for 2 to 3 days. The expected glucoamylase-hirulog product of these transformants consisted of glucoamylase catalytic core and linker region, followed by a KEX2 cleavage site (Lys-Arg), five tandem repeats of R3-hirulog (each separated by a lysine residue), and ending with a lysine and five histidine residues at the carboxyl terminus. Cleavage by KEX2 within the secretory apparatus of Aspergillus was expected to cleave this fusion protein to release a truncated form of glucoamylase (i.e., the catalytic core and linker region; being the same size as the glucoamylase produced by GAP3-4GAΔ3' #2) and a 100 amino acid fragment containing the five tandem repeats of R3-hirulog and the terminal five histidine residues. Three extra protein bands with apparent molecular weights of approximately 58 kDa, 44 kDa, and 10.8 kDa which were not observed in samples from untransformed control strains, were observed in supernatant samples from GAP3-4GAKR(KHi$_5$)H+ #7 and dgr246GAKR(KHi$_5$)H+ #14 after SDS-PAGE and Coomassie staining. We concluded that only a proportion of the glucoamylase-(hirulog)$_5$ fusion protein was cleaved by KEX2 so that a full-length form of glucoamylase-(hirulog)5 the expected truncated form of glucoamylase and a polypeptide containing five repeats of R3-hirulog were present. Purification of proteins bearing a polyhistidine tail from culture supernatant of these transformants was performed using Ni-NTA columns. Two purified proteins could be eluted from these columns; one of approximately 58 kDa and thus representing the fill-length glucoamylase-(hirulog)$_5$ fusion, and one of approximately 10.8 kDa which was in good agreement with the predicted size of the 100 amino acid polypeptide containing five tandem repeats of R3-hirulog.

The smaller polypeptide (10.8 kDa) was purified by HPLC from the mixture of two proteins purified above using Ni-NTA columns from culture supernatant of dgr246GAKR (KHi$_5$)H+ #14. The amino terminal sequence was determined to be GGGGN (SEQ ID NO: 39); i.e., it began with the third residue of R3-hirulog instead of the first residue as expected. Mass spectrometry was used to accurately determine the molecular weight of this polypeptide. A size which was consistent with the expected sequence of 100 amino acids minus the first two residues was determined. Thus, it was concluded that the expected 100 amino acid tandem repeat of R3-hirulog was released by the action of KEX2 proteinase from the glucoamylase-(hirulog)$_5$ protein, and that this polypeptide presumably lost the first two amino acid residues as a result of aminopeptidase action.

Trypsin was used to digest separately the 10.8 kDa and 58 kDa proteins which had been purified on Ni-NTA columns from culture supernatant of strain dgr246GAKR(KHi$_5$)H+ #14. The peptide fragments which were generated were separated by HPLC. A peptide which was generated from both the 10.8 kDA and 58 kDa proteins was identified and collected. Mass spectrometry analysis determined a molecular weight for this peptide which was consistent with R3-hirulog. The amino acid sequence of the amino-terminus of this peptide was determined as RPGGN (SEQ ID NO: 40), confirming that it was R3-hirulog.

The glucoamylase-hirulog fusion proteins produced either by transformant dgr246GA(KHi)$_5$+ #11 after 3 days or by GAP3-4GA(KHi)$_5$+ after 2 days in Sheftone N medium was identified on Coomassie stained SDS-polyacrylamide gels by comparison with supernatant samples from untransformed control strains. The glucoamylase-(hirulog)$_5$ protein from these transformants was estimated to be 55 kDa, approximately 8 kDa larger than the truncated glucoamylase produced by transformant GAP3-4GAΔ3' #2 (47 kDa). This difference in size corresponds approximately to the expected size (95 amino acids, 10.2 kDa) of five repeats of R3-hirulog which were expected to be attached to the glucoamylase protein at the same position (amino acid 498) at which the glucoamylase product is truncated in transformant GAP3-4GAΔ3' #2.

EXAMPLE 4

Construction of the pG Plasmid Series, a Series of Expression Vectors Containing Polypeptide-encoding Sequences Fused to the Catalytic Region of Glucoamylase A series of expression plasmids (the pG series) was constructed, using methods known in the art, designed to produce fusion proteins consisting of desired polypeptides used to the C-terminus of the catalytic region of Aspergillus glucoamylase. The expression cassette in this plasmid series contained the promoter and 5' flanking region of the glaA gene; the coding region of the glaA from the start codon to an engineered NheI site immediately after codon number 468; a synthetic piece of double stranded DNA encoding the desired peptide with NheI and BstEII ends; the terminator region of glaA; the A. niger pyrG gene; and the 3' flanking DNA from the glaA gene.

To construct the pG series of plasmids it was first necessary to introduce an NheI site at the desired position within the glucoamylase coding region. To do this we made use of the fact that there is a naturally occurring DraIII restriction site which interupts the glucoamylase coding region at the codon for amino acid 465 of mature glucoamylase. A plasmid derived from pGAKHi+ was cut with DraIII (see FIG. 9), the DNA ends were dephosphorylated by the action of alkaline phosphatase, and the larger of the two fragments containing the glaA promoter and most of the glaA coding region was purified. In a separate reaction the same plasmid was cut with DraIII plus NheI and the second to largest DNA fragment containing the glaA terminator and pyrG was purified. These two purified DNA fragments were ligated along with the synthetic piece of double stranded DNA obtained by annealing the following complementary oligonucleotides which had been phosphorylated at their 5' ends. The seqences of the two oligonucleotides were 5'-GTGGCCGAGTG-3' (SEQ ID NO: 41) and 5'-CTAGCACTCGGCCACGAG-3' (SEQ ID NO: 42).

The above ligation created the plasmid pGHi (FIG. 10) which encodes a fusion protein consisting of the prepro regions of glucoamylase, mature glucoamylase residues 1–468, and R3-hirulog. Plasmid pGHi contains unique NheI and BstEII sites which can be utilized to insert a DNA fragment encoding any other desired polypeptide such that a fusion protein (comprising the glucoamylase catalytic region and the desired peptide) would be expected to be produced after transformation into Aspergillus strains.

Plasmid pGHi was digested with NheI and BstEII, the DNA ends were dephosphorylated with alkaline phosphatase and the large DNA fragment was purified. Plasmid pK1,K2X4,3 was cut with NheI and BstEII and the small fragment of DNA encoding five tandem repeats of R3-hirulog was purified. These two fragments of DNA were ligated to form pG(KHi)$_5$ (FIG. 10).

Plasmids pGHi and pG (KHi)$_5$ were transformed into strains GCGAP3-4 or dgr246 P2 and the transformants were screened for glucoamylase production as described in the General Methods section. The following transformants were selected for further study.

GAP3-4G(Hi)$_5$ #3 dgr246GHi #5 dgr246G(Hi)$_5$ #7

The glucoamylase-hirulog fusion protein produced by transformants dgr246GHi #5 and dgr246G(Hi)$_5$ #7 after 3 days, and by GAP3-4G(Hi)$_5$ #3 after 2 days, in Sheftone N medium was identified on Coomassie stained polyacrylamide gels by comparison with supernatant samples from untransformed control strains. As judged by electrophoresis, the protein from dgr246G(Hi)$_5$ #7 and GAP3-4G(Hi)$_5$ #3 was approximately 59 kDa, which was 8 kDa larger than that from dgr246GHi #5 at approximately 42 kDa. This difference in size corresponds to approximately the expected size (76 amino acids, 8.2 kDa) of four additional repeats of R3-hirulog attached to the glucoamylase-(hirulog)$_5$ protein.

EXAMPLE 5

Construction of the pGAXS Plasmid Series, a Series of Expression Vectors Containing Polypeptide-encoding Sequences Inserted into the Linker Region of Glucoamylase A series of expression plasmids (the pGAXS series) was constructed, using methods known in the art, designed to produce fusion proteins consisting of desired polypeptides inserted into the linker region of full-length Aspergillus glucoamylase. The expression cassette in this plasmid series contained the promoter and 5' flanking region of the glaA gene; the complete coding region of the Aspergillus glaA gene with a synthetic piece of double stranded DNA (with NheI sites at both ends) encoding the desired peptide inserted into the naturally occurring NheI restriction site at codons 497 and 498; the terminator region of glaA; the *A. niger* pyrG gene; and the 3' flanking DNA from the glaA gene.

The construction of this series of plasmids proceeded as follows. An approximately 340 bp fragment of DNA was isolated which represents the 3' end of the glaA coding region from an NheI site at codons 497 and 498 of mature glucoamylase to a BstEII site 20 bp 5' of the translation stop codon which is present in the *A. niger* strain #7 glaA. Plasmid pGAKHi+ was digested with NheI and BstEII, the DNA ends were dephosphorylated, and the larger of the two fragments generated was purified. The above two DNA fragments were ligated to produce plasmid pGApyrGV which contains the complete glaA coding region with a unique NheI site within the portion encoding the glucoamylase linker region.

Plasmid pGApyrGV was digested with NheI and the DNA ends were dephosphorylated. Plasmid pK1,3K was cut with NheI and the small fragment of DNA encoding R3-hirulog was purified. These two fragments of DNA were ligated to form pGAHiS (FIG. 11). DNA sequence analysis confirmed that the peptide-encoding DNA fragment was inserted in the desired orientation.

Similarly, the NheI fragment of synthetic DNA encoding the HA epitope was isolated from plasmid pEpiN and inserted into the NheI site of pGApyrGV to create pGAepiS (FIG. 11). DNA sequence analysis confirmed that the peptide-encoding DNA fragment was inserted in the desired orientation.

Plasmids pGAHiS and pGAepiS were transformed into strain GCGAP3-4 and the transformants were screened for glucoamylase production as described in the General Methods section. The following transformants were selected for further study.

GAP3-4GAHiS #3

GAP3-4GAepiS #1

The glucoamylase-hirulog fusion protein produced by GAP3-4GAHiS #3 grown in Sheftone N medium was identified on Coomassie stained polyacrylamide gels by comparison with supernatant samples from untransformed control strain. This glucoamylase-hirulog product appeared to be similar to native *A. niger* glucoamylase product in that two protein bands were observed which were estimated to be 69 and 54 kDa in size. In this example, a single copy of R3-hirulog has been inserted into the linker of full-length glucoamylase. Since a protein the size of full-length glucoamylase was produced, it is clear that the embedded hirulog was also present in the fusion protein.

The glucoamylase-HA epitope produced by GAP3-4GAepiS #1 grown in Clofine medium for 3 days was detected on Western blots. As with the product of GAP3-4GAHiS #3 above, the glucoamylase-HA epitope product appeared similar to the native glucoamylase product in that forms of the protein of a similar size to GAI and GAII were observed on Coomassie stained SDS-polyacrylamide gels. Both the larger and the smaller form of glucoamylase-HA epitope were detectable using the anti-HA antibody.

EXAMPLE 6

Construction of pEpiGA, an Expression Vector Containing a Polypeptide-encoding Sequence Fused to the Amino Terminus of Glucoamylase An expression plasmid (pEpiGA) was designed to produce a fusion protein consisting of the HA epitope fused to the N-terminus of residues 1–498 of mature Aspergillus glucoamylase. The expression cassette in this plasmid contained the following components: the promoter and 5' flanking region of the glaA gene; the coding region for the prepro regions of glucoamylase; a synthetic piece of double stranded DNA inserted at a BssHII site encoding alanine, lysine, arginine, the HA epitope peptide, and a methionine residue; the coding region for residues 1–498 of mature glucoamylase, the terminator region of the glaA gene; the *A. niger* pyrG gene; and the 3' flanking DNA from the glaA gene.

The construction of this plasmid proceeded as follows. A plasmid derived from the pGA+ series was digested with HindIII and SphI and a DNA fragment of approximately 2.2 kb was purified from an agarose gel. This fragment contains the glaA promoter and the first approximately 1 kb of the coding region of glaA. Within this fragment the naturally occurring BssHII cleavage site at the end of the coding region for the glucoamylase proregion is unique. Plasmid pLitmus38 (New England Biolabs) was digested with HindIII and SphI, the DNA ends were dephosphorylated with alkaline phosphatase, and the large DNA fragment was purified from an agarose gel. These two DNA fragments were ligated to form pLitGA5'.

Plasmid pLitGA5' was digested with BssHII, was dephosphorylated with alkaline phosphatase and the DNA fragment was purified. Plasmid pLit29+Nepi was digested with BssHII and the 42 residue oligonucleotide was purified from an agarose gel. These two DNA fragments were ligated to form pGA5'+Nepi. DNA sequence analysis confirmed that a single oligonucleotide had been inserted into the glaA coding region in the desired orientation.

Finally, pGA5'+Nepi was digested with HindIII and SphI and the DNA fragment containing the glaA promoter and first 1 kb of coding region with inserted oligonucleotide was purified from an agarose gel. Plasmid pGAΔ3' was digested with HindIII and SphI and the largest resulting DNA fragment (containing the rest of the glaA coding region, the glaA terminator region and the inserted pyrG gene) was purified. Plasmid pGAΔ3' was digested with HindIII, the DNA ends were dephosphorylated, and smaller of the two resulting DNA fragments (comprising the pSL1180 vector) was purified. These three DNA fragments were ligated to form pEpiGA (FIG. 12).

The amino acid sequence of the glucoamylase produced by Aspergillus transformants harboring this expression vector would be expected to consist of the authentic signal sequence (which would be removed upon entry into the endolasmic reticulum of the cell), the authentic prosequence (which would be removed within the secretory apparatus of the cell by KEX2-mediated cleavage), alanine, lysine and arginine residues (which should also be removed within the secretory apparatus of the cell by KEX2), HA epitope followed by a methionine residue (which could be cleaved on the C-terminal side by cyanogen bromide treatment to release the epitope with attached methionine) and residues 1–498 of mature glucoamylase.

Plasmid pEpiGA was transformed into strain dgr246 P2 and the transformants were screened for glucoamylase production as described in the General Methods section. The following transformant was selected for further study.

dgr246 EpiGA #12

Transformant dgr246 EpiGA #12 was cultured in Sheftone N medium for 3 days. Western analysis using the anti-HA antibody demonstrated the presence of the HA epitope-glucoamylase fusion protein.

EXAMPLE 7

Construction of Vectors for Expression of CBHI-hirulog Fusion Proteins in *Trichoderma longibrachiatum*

*T. longibrachiatum* cellobiohydrolase I, CBHI, is a secreted protein which has a 17 amino acid secretion signal sequence and a mature protein of 496 amino acids. The mature protein is composed of two separately folded domains, the catalytic core comprising residues 1–437 and the cellulose binding domain (CBD) comprising residues 461–496. These two domains are separated by a linker region, residues 434–460.

The cbhl gene (encoding CBHI) has been cloned previously (Shoemaker et al., 1983, Bio/Technology 1: 691–696). The entire coding region for CBHI was subcloned from genomic DNA as an approximately 1.75 kb SstII-XmaI fragment into SstII-XmaI digested pSL1180. The SstII site exists 15 bp 5' of the translation start codon and the XmaI site exists 76 bp 3' of the translation stop codon. The resulting subclone was designated as pEN601.

Vector pEN601 was modified by replacing the CBHI cellulose binding domain (CBD) encoding region with the restriction enzyme sites for NheI and BstEII to allow subsequent insertion of the peptide encoding sequences. In addition, a naturally occurring BstEII site in the DNA encoding the C-terminal portion of the catalytic core region of CBHI was inactivated. All these alterations were done in a single step. The vector pEN601 was digested with BstEII, which cleaved the vector within the cbhl sequence. This BstEII-cut DNA was treated with mung bean nuclease to trim the single-stranded DNA ends resulting in blunt ends and destruction of the BstEII site. This linear, blunt-ended pEN601 was further digested with AgeI, which cuts within the cbhl transcription terminator at a position 23 bp 3' to the stop codon, resulting in removal of the sequences coding for the CBD.

A DNA fragment was made by PCR amplification of cbhl template DNA with primers pep1 and pep2. The 37-mer pep1 primer coded for a PmlI site (after cleavage with PmlI the blunt-ended DNA produced was designed to be ligated with the blunted BstEII site mentioned above) followed by codons for the approximately 8 amino acids which naturally exist 3' to the BstEII site in the DNA encoding CBHI. The codon usage for the first two amino acids after the BstEII site, valine and threonine (residues 416 and 417 of mature CBHI), was designed to be altered from GTC to GTG and ACC to ACT, respectively, in order to not recreate the BstEII recognition site. These changes would not have altered the amino acid sequence in this part of CBHI. However, after PCR it was observed by DNA sequence analysis that the first codon after the BstEII site had been changed from GTC to GCG, changing amino acid number 416 of mature CBHI from valine to alanine. The 53-mer pep2 primer had 23 nt at the 3' end which were complementary to the end of the cbhl linker region (up to codon number 459 of mature CBHI) with NheI and BstEII sites for subcloning of polypeptide encoding sequences at the end of the cbhl linker region. The 51 end of pep2 had an AgeI cleavage site for insertion of the PCR-generated fragment (170 bp) into pEN601. The primer sequences were as follows.

pep1: 51-CTT CAC ACG TGA CTT TCT CCA ACA TCA AGT TCG GAC C (SEQ ID NO: 43).

pep2: 51-AAT CTA CCG GTG GTC ACC GCG CTT GCT AGC TCC GGG AGA GCT TCC AGT GGT AG (SEQ ID NO: 44).

The PCR amplified 170 bp insert was digested with PmlI and AgeI and cloned into BstEII and AgeI digested pEN601, of which the BstEII site was blunt-ended as described above. The resultant vector, carring the modified cbhl sequence, was designated as pEN602.

R3-Hirulog encoding sequences were excised from pK1, K2x4,3 and pA3 (see Example 1) by digestion with NheI and BstEII and were ligated into NheI-BstEII cut pEN602. The resultant vector, with a coding sequence for CBHI (catalytic core and linker regions)-five repeats of R3-hirulog was designated as pEN603 (5.1 kb) and the vector for the shorter fusion protein, i.e., with a single R3-hirulog unit, instead of five, was designated as pEN604 (4.9 kb) (FIG. 3). In each case, the DNA encoded CBHI up to residue 459, followed by alanine and serine residues. The R3-hirulog peptides were separated from CBHI and from each other by lysine residues.

A Trichoderma expression vector, pTIC, was assembled by methods known in the art so that the following components were present as an expression cassette which could be excised from the plasmid by EcoRI digestion (FIG. 14). The expression cassette was located between the EcoRI sites of pSP73 (Promega). The components of the expression cassette were the cbhI5'flanking region and promoter sequences from an EcoRI site approximately 2 kb 5' to the translation start codon to the SstII site 15 bp 5' to the translation start codon; a synthetic piece of DNA encoding an end compatible with SstII digested DNA, a PmeI restriction site and an end compatible with XmaI digested DNA; the cbhI 3' flanking region from the XmaI site 76 bp 3' of the translation stop codon to a BglII site approximately 1.25 kb 3' to the translation stop codon; a synthetic piece of DNA with one end compatible with BglII digested DNA and the other end compatible with NheI digested DNA; the *T. longibrachiatum* pyr4 gene on a 1.7 kb NheI to SphI DNA fragment (Smith et al., 1991, Curr. Genet. 19: 27–33); a synthetic piece of DNA with one end compatible with SphI digested DNA and the other end compatible with BglII DNA; the cbhI3' flanking region from the BglII site approximately 1.25 kb 3' to the cbhI translation stop codon to a PstI site approximately 2.6 kb 3' to the translation stop codon; part of the multiple cloning site of pSL1180 from the PstI site to the EcoRI site. An SstII site naturally occurs within the coding region of the pyr4 gene at around codon number 251. This site had been altered (codon 251 changed from CGC to CGA) by site directed mutagenesis so that it was no longer recognized by SstII but without changing the encoded amino acid sequence.

pTIC was digested with SstII and PmeI, which are adjacent sites and open the vector between the cbhI promoter and terminator sequences for the subsequent insertion of desired peptide coding sequences. The coding sequences for CBHI+5 R3-hirulog units and CBHI+single R3-hirulog unit were cut from pEN603 and pEN604, respectively, by SstII-SmaI double digestion. The Trichoderma expression vector for the longer fusion protein (i.e. with 5 R3-hirulog units) was designated as pEN605 and the expression vector for the CBHI-single R3-hirulog unit as pEN606 (FIG. 15).

EXAMPLE 14

Construction of a Vector for Expression of CBHI-hemagglutinin Epitope Fusion Protein in *Trichoderma longibrachiatum*

A Trichoderma expression vector for production of CBHI (catalytic core and linker region)-hemagglutinin (HA) epitope was constructed in two steps. In the first step the epitope coding sequence, isolated from pEpiNR digested with NheI and BstEII, was ligated into pEN602 which was opened by NheI and BstEII. This first vector carying the coding sequence for CBHI-HA epitope was designated as pEN701 (FIG. 13). In the second and final step the CBHI-HA epitope insert was obtained from pEN701 by SstII and SmaI digestion and ligated into SstII-PmeI opened pTIC (FIG. 14). This Trichoderma expression vector for production of CBHI-HA epitope under control of the cbhI promoter was designated as pEN702 (FIG. 15).

EXAMPLE 15

Transformation of *Trichoderma longibrachiatum*

The *T. longibrachiatum* host strain used for polypeptide expression was *T. longibrachiatum* strain 1A52P13, which was derived from strain RL-P37 by inactivating the genes for all major cellulases; CBHI, CBHII, EGI and EGII. This strain requires exogenous uridine for growth due to inactivation of the pyr4 gene.

The host strain, 1A52P13, was cultivated overnight in Vogel's medium supplemented with 2 mg/ml uridine and 1% glucose. Mycelium was centrifuged in 50 ml conical tubes in a clinical centrifuge in full speed for 10 minutes and washed twice with 1.2 M $MgSO_4$, 10 mM Na-phosphate, pH 5.8 and the supernatant was discarded. The washed mycelium was resuspended in Novozyme solution [200 mg of Novozym 234 (Interspex Products, Foster City, Calif.) in 40 ml of 1.2 M $MgSO_4$, 10 mM Na-phosphate, pH 5.8; filter-sterilized]. The mycelial suspension was shaken in Novozyme solution at 150 rpm on an orbital shaker at 28° C. for 1 to 1.5 h, and formation of protoplasts was monitored using a microscope. After the incubation, the protoplast solution was poured into sterile, clear Oakridge tubes, filling the tubes half full. One volume of 0.6 M sorbitol, 0.1 M Tris-HCl, pH 7.0 was pipetted slowly on top of the protoplast suspension. The tubes were centrifuged, without brakes, in an HB-4 rotor (Sorvall) at 4000 rpm, for 15 minutes, at 4° C. Protoplasts, which formed a cloudy layer between the two phases, were collected into clear Oakridge tubes using plastic, disposable Pasteur pipettes. The protoplast suspension was mixed with one volume of 1.2 M sorbitol buffer (1.2 M sorbitol, 10 mM $CaCl_2$, 10 mM Tris-HCl, pH 7.5) and centrifuged in an HB-4 rotor at 4500 rpm, for 5 minutes. Protoplasts were washed once more with 4–6 ml of 1.2 M sorbitol buffer. The protoplast pellet was resuspended in 300–1000 µl of 1.2 M sorbitol buffer and protoplasts were counted using a hemocytometer. Protoplasts were diluted to yield $10^7$–$10^8$ protoplasts per ml of buffer. 20 µl of DNA in TE buffer (TE was used as a control) was mixed with 200 µl of protoplast suspension, followed by addition of 50 µl of PEG solution (25% PEG 6000, 50 mM $CaCl_2$, 10 mM Tris-HCl, pH 7.5). This transformation mixture was placed on ice for 20 minutes. After incubation on ice, 2 ml of PEG solution was added, followed by 4 ml of 1.2 M buffer. This transformed protoplast solution (in 100, 500 or 1000 µl aliquots) was added to melted soft agar medium (Vogel's) and poured on Vogel's plates. Both the soft agar and plates were osmotically stabilized by 1.2 M sorbitol. Plates were incubated at 30° C.

Transformation of *T. reesei* 1A52P13 with pEN605 resulted in two transformants expressing CBHI-hirulog(5 units) fusion protein. These transformants were designated as 605.5 and 605.23. Transformation with pEN606 resulted in five strains (606.9, 606.15, 606.17, 606.24 and 606.25) which produced CBHI-hirulog (1 unit) fusion protein. Transformants shown to produce CBHI-hemagglutinin epitope were designated as 702.1, 702.6 and 702.10. The best transformants, as determined by the intensities of the product in Commassie stained gel, were analysed further.

EXAMPLE 16

Cultivation of Peptide-producing Transformants of *Trichoderma longibrachiatum*

Transformants were maintained on Vogel's medium. Baffled shake flasks with 50 ml of either lactose or Proflo medium were inoculated with agar blocks of fungal culture. The lactose medium consisted of (g/l): lactose 10.0; peptone 2.0; yeast extract 1.0; $KH_2PO_4$ 15.0; $(NH_4)_2SO_4$ 2.0; $MgSO_4.7H_2O$ 0.3; $CaCl_2.2H_2O$ 0.3; trace metal stock solution 1.0 ml/l. Proflo medium is composed of (g/l): Proflo 22.5; lactose 30.0; $(NH_4)_2SO_4$ 6.5; $KH_2PO_4$ 2.0; $MgSO_4.7H_2O$ 0.3; $CaCl_2$ 0.2; $CaCO_3$ 0.72; trace metal stock solution 1.0 ml/l and 10% Tween 80 2.0 ml/l . The trace metal stock solution used in both media had (g/l): $FeSO_4.7H_2O$ 5.0; $MnSO_4.H_2O$ 1.6; $ZnSO_4.7 H_2O$ 1.4; $CoCl_2.6 H_2O$ 2.8.

Transformants were cultivated for six days at 30° C. and samples were drawn daily for analysis. Culture supernatants were analyzed using Coomassie stained SDS-PAGE and Western analysis as described for analysis of Aspergillus supernatants. The supernatant samples were concentrated approximately four fold using Centricon-10 (Amicon) concentrators.

It was possible to identify the CBHI-polypeptide fusion proteins produced by transformants by comparison with culture supernatant from strain 1A52P13, which produced no CBHI protein, or from a strain of *T. reesei* deleted for the genes encoding EGI and EGII, which produced native CBHI protein. Samples of supernatant from the R3-hirulog-producing strains 605.5 and 606.17 were analyzed by SDS-PAGE. The CBHI protein product from 16 hour-old cultures of both 605.5 and 606.17 had a higher molecular weight as determined by SDS-PAGE than the CBHI protein from later timepoints, which were of the same size as native CBHI from the control strain. This reduction in size after the first day of cultivation was particularly clear for the fusion protein carrying five R3-hirulog units, because this fusion protein was 6.5 kD larger than CBHI. This visible reduction in size, observed by the second day of culture, suggested degradation of the fusion protein.

Supernatant samples from the CBHI-hemagglutinin epitope producing transformant 702.1 from different timepoints during culture were run on SDS-PAGE, blotted on nitrocelluose and analyzed with the monoclonal antibody specific to hemagglutinin epitope. A signal was observed in samples taken after 16 hours of culture. However, a weaker signal was observed with samples from 2 day old cultures and no signal was observed from the third day of culture and beyond, even though a Coomassie stained gel showed that the later samples contained a protein product the same size as CBHI.

What is claimed is:

1. A fusion polypeptide comprising, from an amino-terminus of said fusion polypeptide, first, second, third and fourth amino acid sequences, said first amino acid sequence comprising a signal polypeptide functional as a secretory sequence in a first filamentous fungus, said second amino acid sequence comprises a secreted polypeptide or functional portion thereof from said first or a second filamentous fungus, said third amino acid sequence comprises a cleavable linker and said fourth amino acid sequence comprises two or more desired polypeptides.

2. A fusion polypeptide comprising, from an amino-terminus of said fusion polypeptide, first, fifth, third and second amino acid sequences, wherein said first amino acid sequence comprises a signal polypeptide functional as a secretory sequence in a first filamentous fungus, said second amino acid sequence comprises a secreted polypeptide or functional portion thereof from said first or a second filamentous fungus, said third amino acid sequence comprises a cleavable linker and said fifth amino acid sequence comprises at least one desired polypeptide.

3. A fusion polypeptide comprising, from an amino-terminus of said fusion polypeptide:
   a) a first amino acid sequence comprising a signal polypeptide functional as a secretory sequence in a first filamentous fungus;
   b) a second amino acid sequence comprising first and second parts and comprising a secreted polypeptide or functional portion thereof normally secreted from said first or a second filamentous fungus; and
   c) an insertion amino acid sequence between said first and second parts comprising a fifth amino acid sequence flanked by third amino acid sequences;
   wherein said third amino acid sequences comprise cleavable linkers and said fifth amino acid sequence comprises at least one desired polypeptide.

4. A fusion polypeptide according to claim 1 wherein said two or more desired polypeptides of said fourth amino acid sequence are the same polypeptide.

5. A fusion polypeptide according to claim 1 wherein at least two of said two or more desired polypeptides of said fourth amino acid sequence are different polypeptides.

6. A fusion polypeptide according to claim 1 wherein said fourth amino acid sequence further comprises at least one cleavable linker, wherein said desired polypeptides are separated by said cleavable linker.

7. A fusion polypeptide according to claim 6 wherein said fourth amino acid sequence comprises at least three desired polypeptides and at least two cleavable linkers, wherein each of said desired polypeptides is separated by one of said cleavable linkers.

8. A fusion polypeptide according to claim 6 wherein said fourth amino acid sequence comprises at least four desired polypeptides and at least three cleavable linkers, wherein each of said desired polypeptides is separated by one of said cleavable linkers.

9. A fusion polypeptide according to claim 7 wherein said fourth amino acid sequence comprises at least four desired polypeptides and at least three cleavable linkers, wherein each of said cleavable linkers is positioned between desired polypeptides.

10. A fusion polypeptide comprising, from an amino-terminus of said fusion polypeptide:
    a) a first amino acid sequence comprising a signal polypeptide functional as a secretory sequence in a first filamentous fungus;
    b) a second amino acid sequence comprising first and second parts and comprising a secreted polypeptide or functional portion thereof from said first or a second filamentous fungus, wherein said secreted polypeptide contains a linker region; and
    c) an insertion amino acid sequence between said first and second parts of said second amino acid sequence comprising a fifth amino acid sequence flanked by third amino acid sequences, wherein the insertion point is within said linker region;
    wherein said third amino acid sequences comprise cleavable linkers and said fifth amino acid sequence comprises at least one desired polypeptide.

11. A fusion polypeptide according to claim 1, 2 or 3 wherein said first amino acid sequence comprises a signal polypeptide or portion thereof selected from the group consisting of signal polypeptides from glucoamylase, α-amylase, and aspartyl protease from Aspergillus species, signal polypeptides from bovine chymosin and human tissue plasminogen activator and signal polypeptides from Trichoderma cellobiohydrolase I and II.

12. A fusion polypeptide according to claim 11 wherein said first amino acid sequence comprises the signal polypeptide from *Aspergillus awamori* glucoamylase.

13. A fusion polypeptide according to claim 1, 2 or 3 wherein said second amino acid sequence comprises a secreted polypeptide selected from the group consisting of glucoamylase, α-amylase, and aspartyl protease from Aspergillus species and Trichoderma cellobiohydrolase I and II.

14. A fusion polypeptide according to claim 13 wherein said second amino acid sequence comprises at least the catalytic domain of glucoamylase from *Aspergillus awamori*.

15. A fusion polypeptide according to claim 13 wherein said second amino acid sequence comprises at least the catalytic domain and part of the linker region of glucoamylase from *Aspergillus awamori*.

16. A fusion polypeptide according to claim 1, 2 or 3 wherein said second amino acid sequence comprises glucoamylase from *Aspergillus awamori*.

17. A fusion polypeptide according to claim 1, 2 or 3 wherein said third amino acid sequence comprises a cleavable linker selected from the group consisting of the prosequence from chymosin, the prosequence of subtilisin, methionine, and sequences recognized by trypsin, factor $X_a$, collagenase, clostripain, subtilisin and chymosin.

18. A fusion polypeptide according to claim 1, 2 or 3 wherein said cleavable linker is a sequence recognized by trypsin.

19. A fusion polypeptide according to claim 18 wherein said sequence recognized by trypsin is a lysine residue.

20. A fusion polypeptide according to claim 18 wherein said sequence recognized by trypsin is lysine-arginine.

21. A fusion polypeptide according to claim 1, 2 or 3 wherein said third amino acid sequence comprises a prosequence of chymosin or a portion thereof.

22. A fusion polypeptide according to claim 1, 2 or 3 wherein said fourth amino acid sequence comprises a desired polypeptide selected from the group consisting of enzymes, hormones, growth factors, cytokines, and serum proteins.

23. A fusion polypeptide according to claim 1, 2 or 3 wherein said fourth amino acid sequence comprises R3-hirulog.

* * * * *